United States Patent
Parihar et al.

(10) Patent No.: US 8,409,216 B2
(45) Date of Patent: Apr. 2, 2013

(54) TISSUE RETRIEVAL DEVICE WITH BUCKLING ARMS

(75) Inventors: Shailendra K. Parihar, Mason, OH (US); Frederick E. Shelton, IV, Hillsboro, OH (US); Haresh D. Patil, Dhule (IN); Mark J. Bookbinder, Blue Ash, OH (US); Wells D. Haberstich, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 408 days.

(21) Appl. No.: 12/692,709

(22) Filed: Jan. 25, 2010

(65) Prior Publication Data
US 2011/0184431 A1 Jul. 28, 2011

(51) Int. Cl.
*A61B 17/22* (2006.01)
(52) U.S. Cl. ........................................................ 606/127
(58) Field of Classification Search .................. 606/110, 606/113, 114, 115, 127, 128, 184; 600/184
See application file for complete search history.

(56) References Cited

U.S. PATENT DOCUMENTS

| | | | |
|---|---|---|---|
| 4,326,530 A | 4/1982 | Fleury, Jr. | |
| 5,368,597 A | 11/1994 | Pagedas | |
| 5,465,731 A | 11/1995 | Bell et al. | |
| 5,480,404 A | 1/1996 | Kammerer et al. | |
| 5,647,372 A | 7/1997 | Tovey et al. | |
| 5,741,271 A | 4/1998 | Nakao et al. | |
| 5,792,148 A * | 8/1998 | Laxvik | 606/131 |
| 5,971,995 A | 10/1999 | Rousseau | |
| 6,409,733 B1 | 6/2002 | Conlon et al. | |
| 2001/0002437 A1 * | 5/2001 | Pagedas | 606/114 |

FOREIGN PATENT DOCUMENTS
WO  WO 01/72205  10/2001

OTHER PUBLICATIONS
International Search Report dated Jul. 20, 2001 for Application No. PCT/US2011/021040.

* cited by examiner

*Primary Examiner* — Ryan Severson
*Assistant Examiner* — Jonathan W Miles
(74) *Attorney, Agent, or Firm* — Frost Brown Todd LLC

(57) ABSTRACT

A specimen retrieval instrument comprises a handle assembly, an actuating rod, an introducer tube, and a retrieval bag. In some versions the instrument includes a fixed arm and a buckling arm that attach to the retrieval bag and that are in communication with the actuating rod. Upon translation of the rod through the tube, the bag may be distally deployed from a proximal position within the introducer tube, and the buckling arm may open the bag for receiving a specimen. In some versions the instrument includes a support arm and a spring loop, with the spring loop attaching to the retrieval bag and the support arm attaching to the spring loop. The support arm and spring loop are in communication with the actuating rod such that movement of the rod deploys the bag from an initial position within the tube and opens the retrieval bag for receiving a specimen.

17 Claims, 17 Drawing Sheets

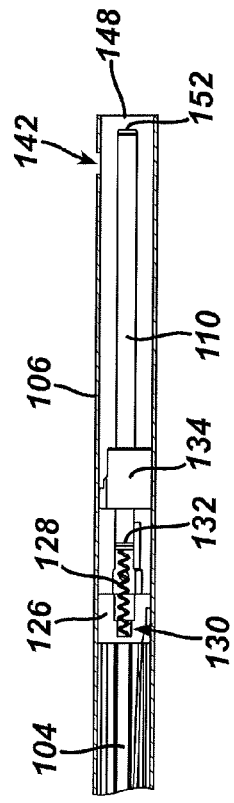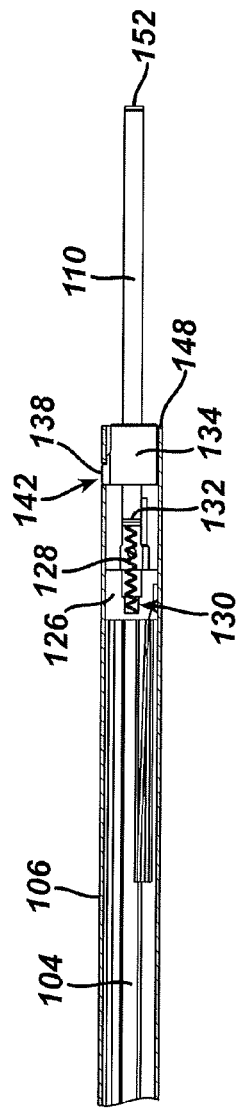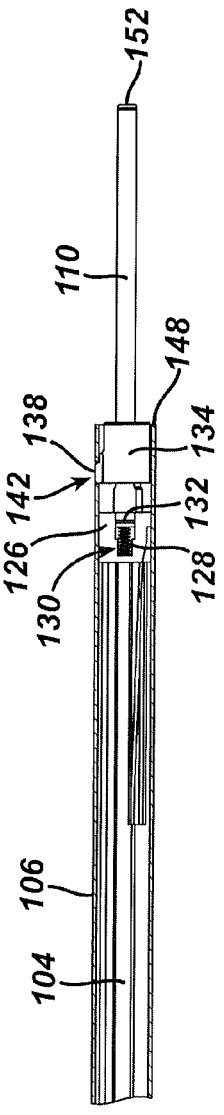

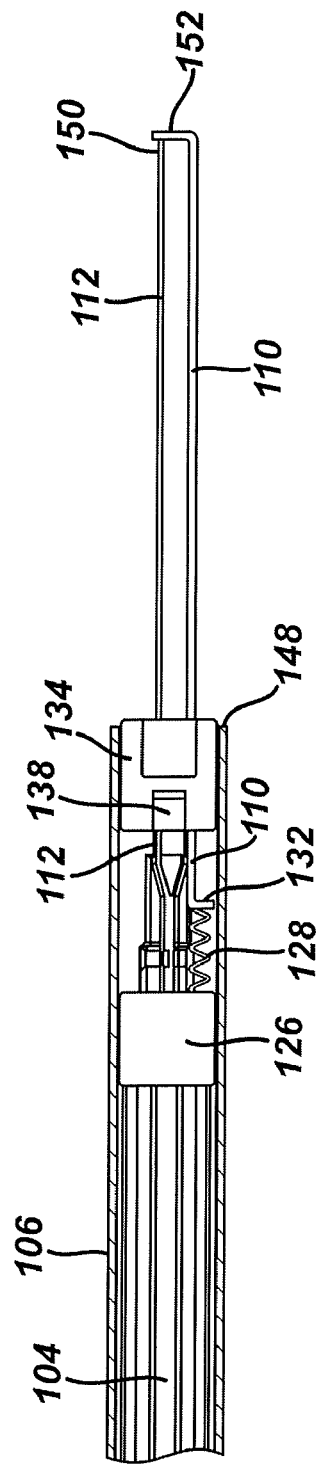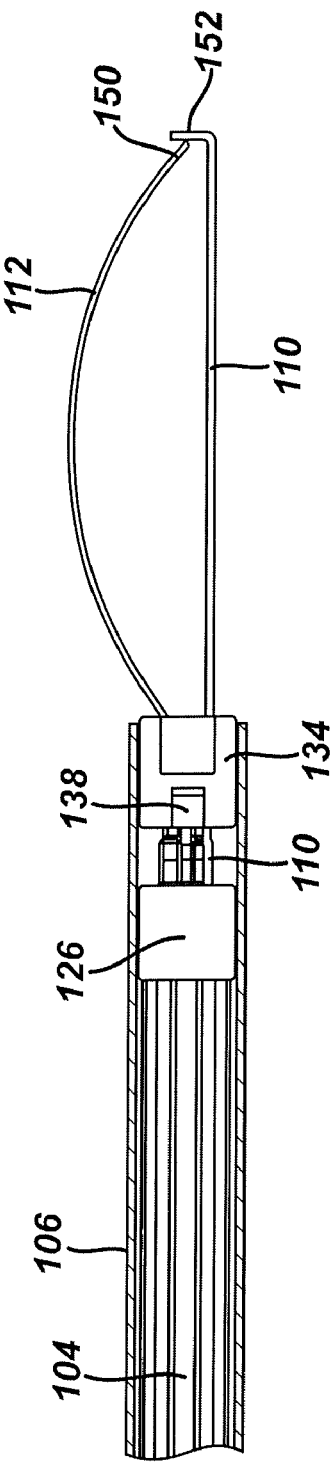

TISSUE RETRIEVAL DEVICE WITH BUCKLING ARMS

BACKGROUND

Endoscopic surgery (e.g., laparoscopy) is a procedure wherein surgery is performed through a series of small openings or incisions in a patient. This type of surgery may reduce or eliminate the need for large incisions and may change some otherwise open surgical procedures such as gall bladder removal to simple outpatient surgery. Consequently, the patient's recovery time may change from weeks to days. These types of surgeries may be used for repairing defects or for the removal of diseased tissue or organs from areas of the body such as the abdominal recess. In some of these procedures, biological material or tissue may be removed or excised from the body through a small opening such as an incision, a small natural orifice, or through a small diameter laparoscopic access port such as a trocar.

Various types of tissue retrieval pouches or bags have been developed to allow for the removal of tissue through a small opening, orifice, or port in an endoscopic surgical procedure. Various instruments have also been devised for introducing, opening, positioning, and closing tissue retrieval bags within a patient; and for removing the bags and enclosed tissue from the surgical site. Some exemplary retrieval bags and associated instruments are disclosed in U.S. Pat. No. 5,465,731, entitled "Specimen Retrieval Pouch and Method for Use," issued Nov. 14, 1995, the disclosure of which is incorporated by reference herein; U.S. Pat. No. 5,480,404, entitled "Surgical Tissue Retrieval Instrument," issued Jan. 2, 1996, the disclosure of which is incorporated by reference herein; U.S. Pat. No. 5,647,372, entitled "Specimen Retrieval Pouch and Method for Use," issued Jul. 15, 1997, the disclosure of which is incorporated by reference herein; U.S. Pat. No. 5,971,995, entitled "Surgical Pouch Instrument," issued Oct. 26, 1999, the disclosure of which is incorporated by reference herein; and U.S. Pat. No. 6,409,733, entitled "Specimen Retrieval Bag," issued Jun. 25, 2002, the disclosure of which is incorporated by reference herein.

While a variety of tissue retrieval devices have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings. In the drawings, like numerals represent like elements throughout the several views.

FIG. 4 is a side view of the distal end of the specimen retrieval instrument of FIG. 1, with the actuating rod in a proximal position, with the introducer tube in cross section, and with the retrieval bag omitted.

FIG. 5 is a side view of the distal end of the specimen retrieval instrument of FIG. 1, with the actuating rod in a first distal position, with the introducer tube in cross section, and with the retrieval bag omitted.

FIG. 6 is a side view of the distal end of the specimen retrieval instrument of FIG. 1, with the actuating rod in a second distal position, with the introducer tube in cross section, and with the retrieval bag omitted.

FIG. 7 is a top view of the distal end of the specimen retrieval instrument of FIG. 1, with the actuating rod in the first distal position, with the introducer tube in cross section, and with the retrieval bag omitted.

FIG. 8 is a top view of the distal end of the specimen retrieval instrument of FIG. 1, with the actuating rod in the second distal position, with the introducer tube in cross section, and with the retrieval bag omitted.

Figure 1:
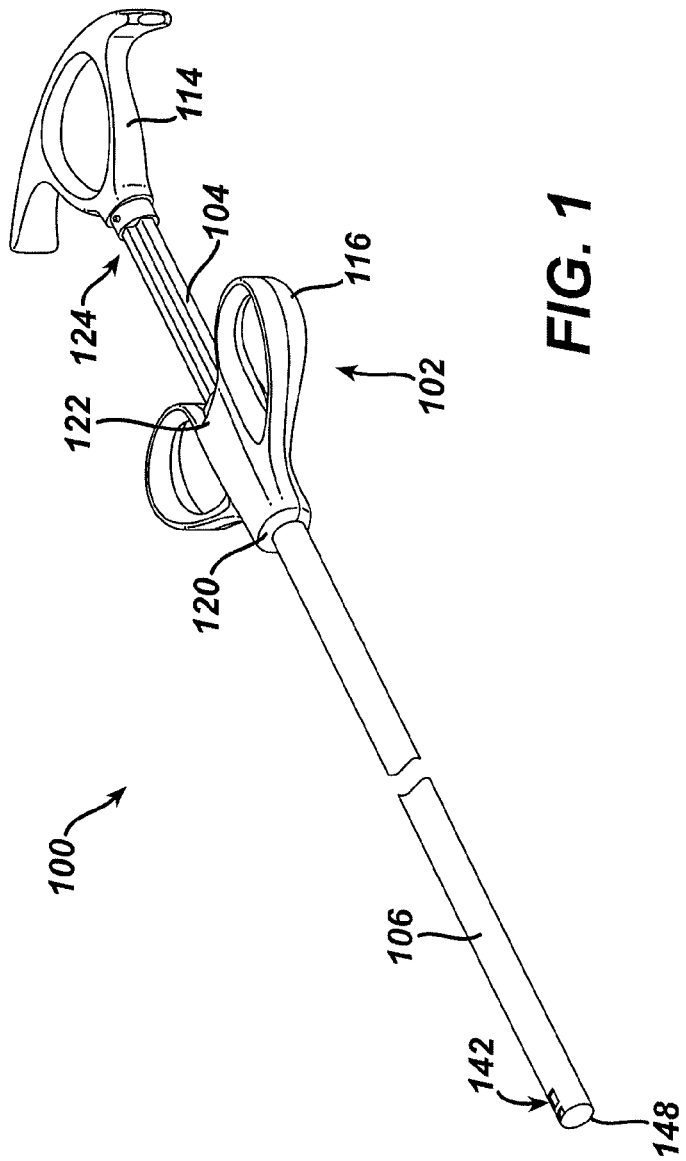
FIG. 1 is a perspective view of an exemplary specimen retrieval instrument having a buckling arm and a retrieval bag, with the retrieval bag in a fully retracted position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples should not be used to limit the scope of the present invention. Other features, aspects, and advantages of the versions disclosed herein will become apparent to those skilled in the art from the following description, which is by way of illustration, one of the best modes contemplated for carrying out the invention. As will be realized, the versions described herein are capable of other different and obvious aspects, all without departing from the invention. Accordingly, the drawings and descriptions should be regarded as illustrative in nature and not restrictive.

I. Exemplary Buckling Arm

A. Exemplary Distal Force Actuation

Figure 2:
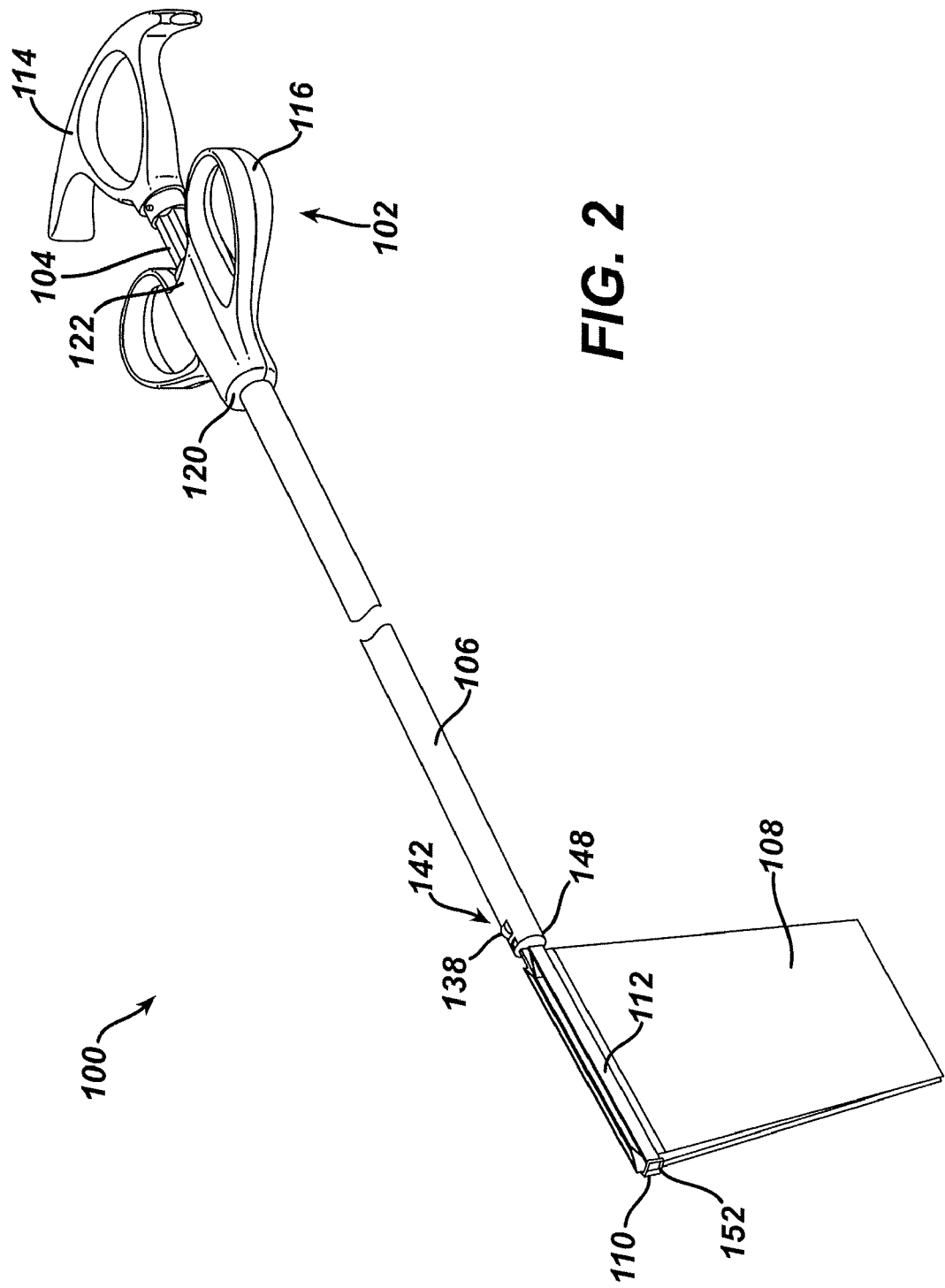
FIG. 2 is a perspective view of the specimen retrieval instrument of FIG. 1, with the retrieval bag in a deployed but closed position.
Figure 3:
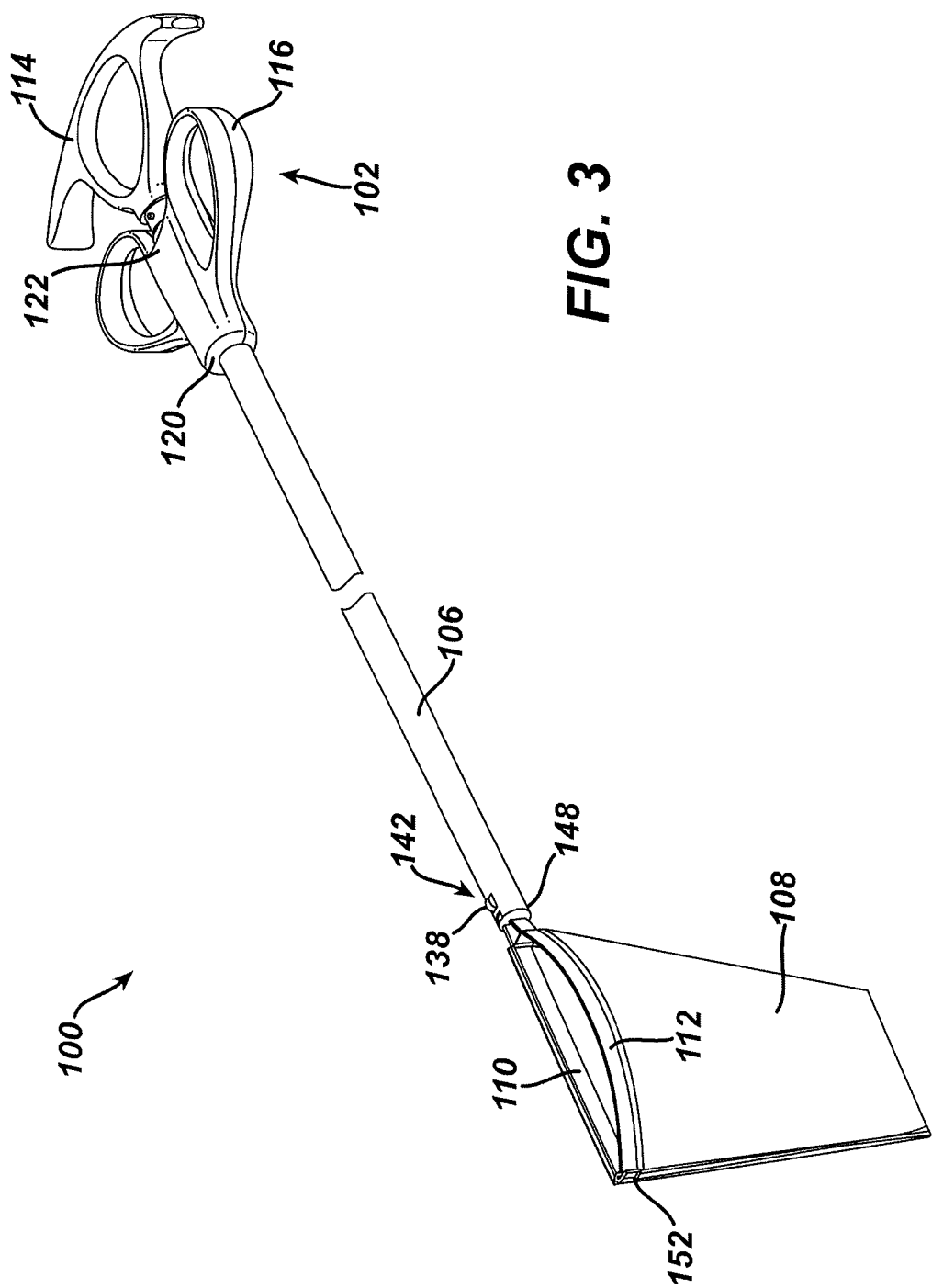
FIG. 3 is a perspective view of the specimen retrieval instrument of FIG. 1, with the retrieval bag in a deployed and opened position.

Referring to FIGS. 1-8, an exemplary specimen retrieval instrument 100 is shown. Specimen retrieval instrument 100 includes handle assembly 102, actuating rod 104, introducer tube 106, plug 134, retrieval bag 108, fixed arm 110, and buckling arm 112. As shown in FIGS. 1-3, handle assembly 102 includes thumb ring 114 and finger rings 116. An internal passageway extends from distal end 120 of finger rings 116 to proximal end 122 of finger rings 116. Actuating rod 104 extends through the passageway, connecting to thumb ring 114 at proximal end 124 of actuating rod 104. Finger rings 116 are connected to introducer tube 106. Thumb ring 114 is moveable relative to finger rings 116 and introducer tube 106, and actuating rod 104 moves in unison with thumb ring 114. In particular, actuating rod 104 is translatable within introducer tube 106. Additional optional features of handle assembly 102 may include markings to indicate directional movement of thumb ring 114 as well as a marking to indicate the orientation of retrieval bag 108—e.g. when locating the open end of retrieval bag 108. Introducer tube 106 of the present example has an open distal end 148 and a lateral opening 142 located proximal to open distal end 148.

Referring to FIG. 1, specimen retrieval instrument 100 is shown in a fully retracted configuration, with actuating rod 104 at a proximal position. In this configuration, retrieval bag 108, fixed arm 110, and buckling arm 112 are located within introducer tube 106. As will be discussed in greater detail below, this configuration is achieved by thumb ring 114 and actuating rod 104 being in a proximal position relative to finger rings 116 of handle assembly 102. When retracted within introducer tube 106, retrieval bag 108 may be rolled up, folded up, wadded up, or have any other suitable configuration within introducer tube 108.

Referring to FIG. 2, specimen retrieval instrument 100 is shown with retrieval bag 108, fixed arm 110, and buckling arm 112 deployed but with retrieval bag 108 closed. As will be discussed in greater detail below, this configuration is achieved by thumb ring 114 and actuating rod 104 being translated distally to an intermediate position, or first distal position, from the proximal position shown in FIG. 1.

Referring to FIG. 3, specimen retrieval instrument 100 is shown with retrieval bag 108, fixed arm 110, and buckling arm 112 deployed and with retrieval bag 108 opened. As will be discussed in further detail below, this configuration is achieved by thumb ring 114 and actuating rod 104 being further extended distally from the intermediate position or first distal position shown in FIG. 2 to a second distal position.

Referring to FIGS. 4-8, actuating rod 104 is positioned within introducer tube 106, and is longitudinally moveable relative to introducer tube 106 by movement of thumb ring 114 as discussed above. Actuating rod 104 includes distal end 126, which is engaged with fixed arm 110 and buckling arm 112. The connection of distal end 126 to buckling arm 112 is such that buckling arm 112 moves in unison with actuating rod 104. The connection of distal end 126 to fixed arm 110 is such that actuating rod 104 may longitudinally move unitarily with fixed arm 110 through a first range of travel, and such that actuating rod 104 may longitudinally move relative to fixed arm 110 through a second range of travel, as discussed further below.

Plug 134 is positioned distal to actuating rod 104. Plug 134 is slidably positioned within introducer tube 106. Plug 134 includes pair of openings (not shown) configured to permit fixed arm 110 and buckling arm 112 to extend through plug 134. Fixed arm 110 is fixedly secured to plug 134. One portion of fixed arm 110 extends distally from plug 134 while another portion of fixed arm 110 extends proximally from plug 134, as will be described in greater detail below. Buckling arm 112 is slidable relative to plug 134. Buckling arm 112 is fixedly secured to distal end 126 of actuating rod 104. As will be described in greater detail below, actuating rod 104, buckling arm 112, plug 134, and fixed arm 110 all translate together relative to introducer tube 106 during initial deployment of retrieval bag 108. However, during opening of deployed retrieval bag 108, actuating rod 104 and buckling arm 112 translate relative to plug 134 and relative to fixed arm 110. In particular, plug 134 and fixed arm 110 remain in a fixed longitudinal position relative to introducer tube 106 when retrieval bag 108 is being opened, as will be described in greater detail below.

Plug 134 further includes a tab 138 projecting upwardly from plug 134. A recess (not shown) is formed below tab 138 in plug 134. Tab 138 is resiliently biased to project upwardly from plug 134, but under sufficient force, tab 138 may be deflected downwardly to occupy at least part of the recess. Tab 138 is configured to secure the longitudinal position of plug 134 within introducer tube 106 by engaging lateral opening 142 in introducer tube 106 when tab 138 is positioned within introducer tube 106 and aligned with opening 142. Tab 138 includes a sloped distal end and a generally square proximal end. The generally square configuration of the proximal end of tab 138 may provide that, once retrieval bag 108 is deployed from within introducer tube 106 (e.g., as shown in FIGS. 2-3), plug 134 cannot be retracted within introducer tube 106 without first depressing tab 138 such that tab 138 occupies its recess and disengages opening 142. The sloped configuration of the distal end of tab 138 allows tab 138 to be pressed downward within the recess by the inner diameter of introducer tube 106 when plug 134 is at a proximal position and during distal movement of plug 134. In some versions, opening 142 of introducer tube 106 may be slightly larger than tab 138 such that further distal or proximal movement of actuating rod 104 may permit slight corresponding distal or proximal movement of plug 134 even when tab 138 is in engagement with opening 142. In some versions, introducer tube 106 may also be provided with a distal locking member (e.g., indentation or inward projection at distal end 148 of introducer tube 106, etc.), which may be configured to abut a distal end of plug 134 such that the distal locking member prevents plug 134 from exiting introducer tube 106 during deployment and opening of retrieval bag 108.

As best seen in FIG. 7, fixed arm 110 of the present example has a proximal L-shaped tab 132 and a distal L-shaped tab 152. Each L-shaped tab 132, 152 projects laterally relative to the longitudinal axis defined by introducer tube 106. In particular, proximal L-shaped tab 132 projects laterally outwardly from the longitudinal axis defined by introducer tube 106; while distal L-shaped tab 152 projects laterally inwardly toward the longitudinal axis defined by introducer tube 106. It should be understood, however, that as with any other component described herein, this configuration of fixed arm 110 is merely exemplary. Fixed arm 110 may have any other suitable configuration as will be apparent to those of ordinary skill in the art in view of the teachings herein.

Retrieval bag 108 is secured to fixed arm 110 and buckling arm 112 in the present example. In particular, retrieval bag 108 is substantially closed when fixed arm and buckling arm 112 are substantially parallel to each other as shown in FIGS. 2 and 7. However, retrieval bag 108 is opened when buckling arm 112 buckles relative to fixed arm 110 as shown in FIGS. 3 and 8 and as will be described in greater detail below. By way of example only, arms 110, 112 may be inserted through one or more sleeves, slots, pockets, loops, slits, etc., formed in retrieval bag 108. Various suitable ways in which retrieval bag 108 may be secured to arms 110, 112 will be apparent to those of ordinary skill in the art in view of the teachings herein.

As shown in FIGS. 4-5, distal end 126 of actuating rod 104 includes a longitudinal recess 130. A coil spring 128 extends within recess 130 and contacts actuating rod 104. Spring 128 is also positioned to contact fixed arm 110, which extends proximally from plug 134. In particular, spring 128 contacts proximal L-shaped tab 132 of fixed arm 110. As noted above, L-shaped tab 132 projects laterally relative to the longitudinal axis defined by introducer tube 106; while spring 128 extends parallel to the longitudinal axis defined by introducer tube 106. In some alternative versions, no portion of fixed arm 110 extends proximally from plug 134, such that proximal L-shaped tab 132 is omitted. In some such versions, the distal end of spring 128 simply contacts the proximal face of plug 134.

In the present example, spring 128 is biased to maintain spatial separation between plug 134 and distal end 126 of actuating rod 104. Spring 128 may also have a spring constant that is sufficient to substantially maintain this spatial separation as actuating rod 104 is moved from a proximal position as shown in FIGS. 1 and 4 to a first distal position as shown in FIGS. 2, 5, and 7, despite any friction between plug 134 and the inner diameter of introducer tube 106. Spring 128 may thus provide substantially unitary translation of plug 134 with actuating rod 104 as actuating rod 104 is moved from a proximal position as shown in FIGS. 1 and 4 to a first distal position as shown in FIGS. 2, 5, and 7. However, upon plug 134 reaching the first distal position, tab 138 of plug 134 snaps into opening 142 of introducer tube 106 in the present example. This engagement between tab 138 and opening 142 restricts further distal movement of plug 134. Accordingly, as actuating rod 104 continues to advance distally in introducer tube 106 (e.g., from the first distal position shown in FIGS. 2, 5, and 7 to the second distal position shown in FIGS. 3, 6, and 8), plug 134 remains substantially stationary in introducer tube 106 and the spring 128 compresses. This additional distal movement of actuating rod 104 relative to plug 134 and introducer tube 106 opens retrieval bag 108 as described in greater detail below. A proximal portion of fixed arm 110 may occupy part of recess 130 as a result of this additional distal movement of actuating rod 104.

In use, specimen retrieval instrument 100 may initially have the arrangement shown in FIGS. 1 and 4, where retrieval bag 108 is disposed within introducer tube 106, and thumb ring 114 and actuating rod 104 are at a proximal position. In this arrangement, the distal portion of specimen retrieval instrument 100 may be inserted within a patient through a suitable incision opening or access port created by a trocar or some other device. By way of example only, introducer tube 106 may present an outer diameter that is between approximately 5 mm (inclusive) and approximately 15 mm (inclusive) (e.g., approximately 10 mm, etc.). Alternatively, introducer tube 106 may have any other suitable dimensions. Once positioned within the patient, retrieval bag 108 may be deployed from within introducer tube 106 by pushing thumb ring 114 distally toward finger rings 116. This action drives actuating rod 104 and plug 134 distally causing retrieval bag 108, fixed arm 110, and buckling arm 112 to emerge from open distal end 148 of introducer tube 106. At about the same time retrieval bag 108 is deployed, tab 138 of plug 134 aligns with opening 142 of introducer tube 106. When aligned, tab 138 engages opening 142 due to tab 138 being resiliently biased to project upwardly from plug 134. Once retrieval bag 108 has been deployed, specimen retrieval instrument 100 may have the arrangement shown in FIGS. 2, 5, and 7.

As shown in FIGS. 2, 5, and 7, with specimen retrieval instrument 100 in position within the patient and having retrieval bag 108 deployed, proximal L-shaped tab 132 of fixed arm 110 contacts spring 128. Also, distal end 150 of buckling arm 112 contacts L-shaped distal end 152 of fixed arm 110. When thumb ring 114 is pushed further distally, actuating rod 104 is driven further distally, and spring 128 compresses between actuating rod 104 and proximal L-shaped tab 132 of fixed arm 110. Compression of spring 128 permits actuating rod 104 to continue distal movement as a proximal portion of fixed arm 110 occupies recess 130 of actuating rod 104.

Buckling arm 112 of the present example is resiliently biased to assume the substantially straight configuration shown in FIGS. 2 and 7. However, the properties of buckling arm 112 are such that buckling arm 112 may buckle or bend away from fixed arm 110. In particular, buckling arm 112 is configured to buckle when distal end 150 of buckling arm 112 bears against L-shaped distal end 152 of fixed arm 110 while sufficient force is applied to buckling arm 112 in a distal direction and while fixed arm 110 remains in a substantially fixed position. When buckling arm 112 buckles or bends away from fixed arm 110, retrieval bag 108 opens. Referring again to FIGS. 3, 6, and 8, at or about the same time as spring 128 compresses, and with distal end 150 of buckling arm 112 bound against L-shaped distal end 152 of fixed arm 110, further distal translation of actuating rod 104 provides a sufficient distal force on buckling arm 112 to cause buckling arm 112 to buckle or bend and thus open retrieval bag 108. Buckling arm 112 may be formed of any suitable material or combination of materials, including but not limited to metal (e.g., stainless steel, nitinol, steel spring alloys, copper spring alloys, etc.), plastic, and/or metal reinforced plastic. Fixed arm 110 may have significantly greater rigidity than buckling arm 112. In particular, fixed arm 110 of the present example has sufficient rigidity to maintain a substantially straight configuration as buckling arm 112 buckles. L-shaped distal end 152 of fixed arm 110 may include a slot, recess, or other feature(s) configured to prevent or reduce the likelihood of disengagement of distal end 150 of buckling arm 112 from L-shaped distal end 152 of fixed arm when buckling arm 112 buckles.

In some versions, retrieval bag 108 is maintained in an open position by thumb ring 114 being configured to remain at a fully distal position. Some such versions may use various biasing or locking means (e.g., releasable ratcheting mechanism, etc.) to accomplish this, while in other versions this may not be necessary. Still in other versions, thumb ring 114 may be biased to seek the intermediate position or first distal position where retrieval bag 108 is deployed but closed. In some such versions it may be necessary to hold thumb ring 114 in its fully distal position to maintain retrieval bag 108 in an open configuration. In any of these versions, when retrieval bag 108 is open, a specimen can be placed within.

Once a specimen has been placed within retrieval bag 108, thumb ring 114 may be retracted proximally, thereby eliminating the force sufficient to maintain buckling arm 112 in the buckled or bent position. In particular, the resilient bias of buckling arm 112 may urge buckling arm 112 back to a substantially straight configuration upon buckling arm 112 being relieved of a distally directed force imposed by actuating rod 104. Thus, retrieval bag 108 may close upon such retraction of thumb ring 114. From this point, specimen retrieval instrument 100, including retrieval bag 108 and specimen, may be removed from the patient.

In some versions, specimen retrieval instrument 100 is configured such that retrieval bag 108 may be removed from specimen retrieval instrument 100 while retrieval bag 108 is within the patient. Some such versions facilitate removal of retrieval bag 108 separate from removal of the other components of specimen retrieval instrument 100. In some versions, this may be accomplished by, among other ways, retrieval bag 108 being removable from arms 110, 112. For instance, in some versions specimen retrieval instrument 100 may include a closure string connected to retrieval bag 108 and having a slipknot attachment to actuating rod 104. Pulling the slipknot loose and retracting the actuating rod 104 may permit detachment of retrieval bag 108 and the closure string from the other components of specimen retrieval instrument 100. In some such versions, a user may pull the closure string to close retrieval bag 108. By way of example only, such a closure mechanism may be configured in accordance with the teachings of U.S. Pat. No. 6,409,733, entitled "Specimen Retrieval Bag," issued Jun. 25, 2002, which is incorporated herein by reference. Still in other versions, it may be feasible to incorporate a closure string with retrieval bag 108, and to release retrieval bag 108 from specimen retrieval instrument 100 such that retrieval bag 108 may be removed from the patient separate from other components of specimen retrieval instrument 100.

While the above description provides adequate disclosure to enable one of ordinary skill in the art to make and use specimen retrieval instrument 100, based on the teachings herein, those of ordinary skill in the art will appreciate that various modifications may provide additional features or functionality. For instance, in some versions, actuating rod 104 may comprise features operable with other features of introducer tube 106 or other components to prevent inadvertent retraction of actuating rod 104 during retrieval bag 108 deployment. For example, actuating rod 104 may include a one way ratcheting mechanism as described in U.S. Pat. No. 6,409,733, entitled "Specimen Retrieval Bag," issued Jun. 25, 2002, which is incorporated herein by reference. Other ways in which inadvertent retraction of actuating rod 104 may be avoided through various features of specimen retrieval instrument 100 will be apparent to those of ordinary skill in the art in view of the teachings herein. Still various other suitable features, components, configurations, and operabilities that may be incorporated into specimen retrieval instrument 300 will be apparent to those of ordinary skill in the art in view of the teachings herein.

B. Exemplary Proximal Force Actuation

Figure 9:
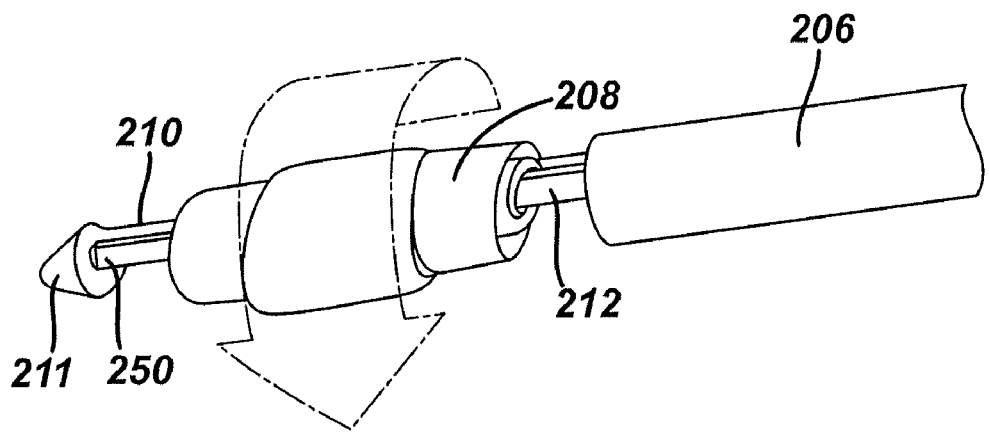
FIG. 9 is a perspective view of another exemplary specimen retrieval instrument, having pair of buckling spring arms and a retrieval bag, with the retrieval bag deployed and wrapped around the spring arms.
Figure 10:
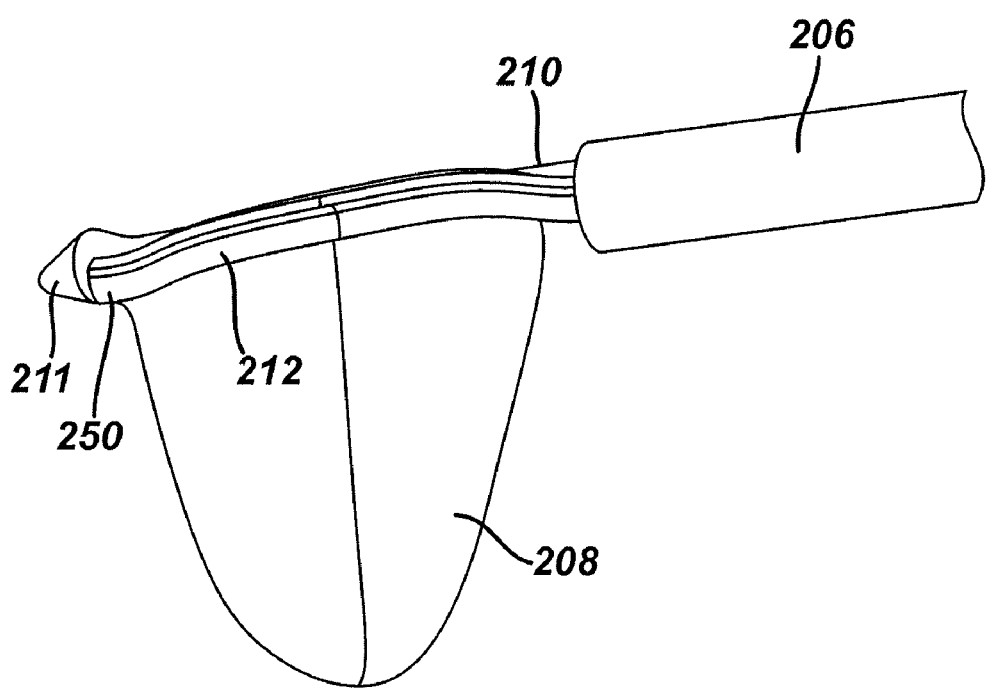
FIG. 10 is a perspective view of the specimen retrieval instrument of FIG. 9, with the retrieval bag deployed and unfurled but not opened.
Figure 11:
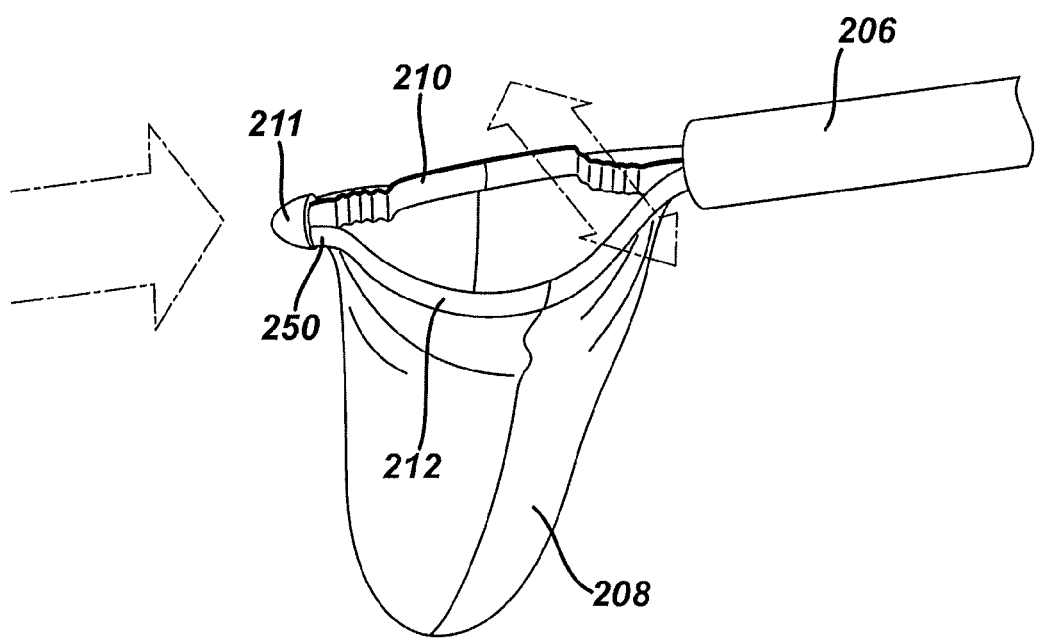
FIG. 11 is a perspective view of the specimen retrieval instrument of FIG. 9, with the retrieval bag deployed, unfurled, and opened.

Referring now to FIGS. 9-11, parts of another specimen retrieval instrument are shown. This alternative specimen retrieval instrument includes an introducer tube 206, a fixed arm 210, a buckling arm 212, and a retrieval bag 208. This alternative specimen retrieval instrument may also include an actuating rod (not shown), a plug (not shown), and a handle assembly (not shown). While not shown in FIGS. 9-11, these other components may be substantially identical to actuating rod 104, plug 134, and handle assembly 102 of specimen retrieval instrument 100 discussed above. Therefore, many details of these other components will not be reiterated, it being understood that such components may be readily incorporated with the components shown in FIGS. 9-11. For instance, a handle assembly and actuating rod may be used to translate arms 201, 212 and retrieval bag 208 from a proximal position to a first distal position. In particular, arms 210, 212 and retrieval bag 208 may be located within introducer tube 206 at the proximal position; and protrude from introducer tube 206 at the first distal position as shown in FIGS. 9-10. Similarly, a handle assembly and actuating rod may be used to transition buckling arm 212 to the buckled position shown in FIG. 11. Various other suitable ways in which components described above in the context of specimen retrieval instrument may be incorporated with the components shown in FIGS. 9-11 will be apparent to those of ordinary skill in the art in view of the teachings herein.

Of course, the alternative specimen retrieval instrument having components shown in FIGS. 9-11 may operate differently in some ways as compared to operation of specimen retrieval instrument 100. For instance, in the present example, and as will be described in greater detail below, retrieval bag 208 is opened by proximal movement of an actuating rod instead of by distal movement of the actuating rod as in specimen retrieval instrument.

Retrieval bag 208 is secured to fixed arm 210 and buckling arm 212 in the present example. In particular, retrieval bag 208 is substantially closed when fixed arm and buckling arm 212 are substantially parallel to each other as shown in FIG. 10. However, retrieval bag 208 is opened when buckling arm 212 buckles relative to fixed arm 210 as shown in FIG. 11 and as will be described in greater detail below. By way of example only, arms 210, 212 may be inserted through one or more sleeves, slots, pockets, loops, slits, etc., formed in retrieval bag 208. Various suitable ways in which retrieval bag 208 may be secured to arms 210, 212 will be apparent to those of ordinary skill in the art in view of the teachings herein.

Referring to FIG. 9, the alternative specimen retrieval instrument of the present example is shown with retrieval bag 208, fixed arm 210, and buckling arm 212 deployed but with retrieval bag 208 wrapped around fixed arm 210 and buckling arms 212. Retrieval bag 208 may be positioned in the wrapped configuration during manufacture and assembly of the specimen retrieval instrument. The wrapping of retrieval bag 208 about arms 210, 212 may assist in positioning retrieval bag 208 within introducer tube 206 when retrieval bag 208 is in a proximal retracted position.

Referring to FIG. 10, the alternative specimen retrieval instrument of the present example is shown with retrieval bag 208, fixed arm 210, and buckling arm 212 deployed and with retrieval bag 208 unfurled. This unfurling of retrieval bag 208 may be accomplished in a variety of ways. For instance, retrieval bag 208 may be unfurled by the surgeon rotating the entire instrument about the longitudinal axis defined by introducer tube 206. In addition or in the alternative, another device (e.g., conventional tissue graspers, etc.) may be used to assist in unfurling of retrieval bag 208. In addition or in the alternative, gravity may be relied on to unfurl retrieval bag 208. In addition or in the alternative, the material properties (e.g., resilience, etc.) of retrieval bag 208 may assist in unfurling of retrieval bag 208. In addition or in the alternative, the actuating rod that was used to distally advance retrieval bag 208 may be rotated relative to introducer tube 206 to assist in unfurling of retrieval bag 208. Still other suitable ways in which retrieval bag 208 may be unfurled will be apparent to those of ordinary skill in the art in view of the teachings herein.

Referring to FIG. 11, the alternative specimen retrieval instrument of the present example is shown with retrieval bag 208, fixed arm 210, and buckling arm 212 deployed and with retrieval bag 208 opened. As will be discussed in further detail below, this may be achieved by an actuating rod being retracted proximally from the distal position shown in FIGS. 9 and 10. Buckling arm 212 may be formed of any suitable material or combination of materials, including but not limited to metal (e.g., stainless steel, nitinol, steel spring alloys, copper spring alloys, etc.), plastic, and/or metal reinforced plastic. Fixed arm 210 may have significantly greater rigidity than buckling arm 212. In particular, fixed arm 210 of the present example has sufficient rigidity to maintain a substantially straight configuration as buckling arm 212 buckles.

In the present example, fixed arm 210 and buckling arm 212 are in communication with an actuating rod that is translatable within introducer tube 206. This relationship is such that the actuating rod may longitudinally move unitarily with buckling arm 212 through a first range of travel, and such that the actuating rod may longitudinally move relative to buckling arm 212 through a second range of travel, as discussed further below. In addition, this relationship is such that the actuating rod longitudinally moves unitarily with fixed arm 210 through both the first and second ranges of travel. Fixed arm 210 includes end cap 211 that is configured to contact distal end 250 of buckling arm 212. Buckling arm 212 is resiliently biased to be immediately adjacent fixed arm 210 at rest or when a force is applied in the distal direction. When buckling arm 212 is immediately adjacent fixed arm 210, retrieval bag 208 is substantially closed. In addition, when buckling arm 212 is immediately adjacent fixed arm 210, buckling arm 212 and fixed arm 210 each have a substantially straight configuration in the present example.

To open retrieval bag 208, the actuating rod is retracted proximally, which causes fixed arm 210 and associated end cap 211 to be pulled in the proximal direction. Buckling arm 212 is inhibited from proximal movement by a plug. For instance, such a plug may be substantially similar to plug 134 described above. In particular, such a plug may be translated distally from a proximal position and then substantially lock in place in a distal position. The proximal end of buckling arm 212 may be substantially secured to such a plug, such that buckling arm 212 translates distally with the plug and then is substantially locked in place with the plug when they reach the distal position.

When a plug and actuating rod are included in the alternative specimen retrieval instrument of the present example, such a plug and actuating rod may have a variety of suitable relationships. For instance, the distal end of such an actuating rod may simply abut a proximal face of such a plug, allowing the actuating rod to push the plug distally while also allowing the actuating rod to be retracted proximally (to pull fixed arm 210 proximally) when the plug is locked in a distal position. To the extent that the actuating rod is rotatable relative to introducer tube (206) (e.g., to assist in unfurling of retrieval bag 208, etc.), at least a portion of the actuating rod or some component secured thereto may be inserted through a central opening or bushing in the plug. In some such versions, buckling arm 212 is also rotatable relative to the plug despite being longitudinally fixed relative to the plug (e.g., an outer bushing on the plug may be secured to buckling arm 212). Other suitable relationships between a plug and an actuating rod will be apparent to those of ordinary skill in the art in view of the teachings herein. Of course, a plug is not even needed. For instance, two longitudinally extending actuating rods may be parallel to each other and extend through introducer tube 206, with one actuating rod being secured to fixed arm 210 and another actuating rod being secured to buckling arm 212. Such actuating rods may be translated distally together, then the actuating rod secured to buckling arm 212 may remain longitudinally fixed in place as the actuating rod secured to fixed arm 210 is retracted proximally. Alternatively, any other suitable components, features, or configurations may be used.

In use, the alternative specimen retrieval instrument of the present example may initially have an arrangement where retrieval bag 208 is disposed within introducer tube 206, and a thumb ring and attached actuating rod (or alternative components) are at a proximal position. The distal portion of the specimen retrieval instrument may be inserted within a patient through a suitable incision opening or access port created by a trocar or some other device. By way of example only, introducer tube 206 may present an outer diameter that is between approximately 5 mm (inclusive) and approximately 15 mm (inclusive) (e.g., approximately 10 mm, etc.). Alternatively, introducer tube 206 may have any other suitable dimensions. Once positioned within the patient, retrieval bag 208 may be deployed from within introducer tube 206 by pushing the thumb ring distally toward finger rings (or some other feature). This action drives the actuating rod distally causing retrieval bag 208, fixed arm 210, and buckling arm 212 to emerge from the open distal end of introducer tube 206, as shown in FIG. 9. Once retrieval bag 208 has been deployed, retrieval bag 208 may be unwrapped from arms 210, 212. Once retrieval bag 208 is deployed and unwrapped, the specimen retrieval instrument may have the arrangement shown in FIG. 10.

As shown in FIGS. 10-11, with the specimen retrieval instrument in position within the patient and having retrieval bag 208 deployed and unwrapped, distal end 250 of buckling arm 212 contacts end cap 211 of fixed arm 210. When the thumb ring (or other feature) is then retracted proximally, the actuating rod (or other feature) also moves proximally. The proximal end of buckling arm 212 remains substantially fixed in place relative to introducer tube 206 at this stage. As the actuating rod moves proximally, fixed arm 210 and associated end cap 211 move proximally thus exerting a proximal force on distal end 250 of buckling arm 212, whose proximal end is longitudinally fixed in place. The properties of buckling arm 212 are such that buckling arm 212 may buckle or bend in a direction away from fixed arm 210 when end cap 211 of fixed arm 210 bears against distal end 250 of buckling arm 212 to provide sufficient proximal force against buckling arm 212. When buckling arm 212 buckles or bends away from fixed arm 210, retrieval bag 208 opens.

In some versions, retrieval bag 208 is maintained in an open position by a thumb ring (or other actuating feature) being configured to remain in a proximal position. Some such versions may use various biasing or locking means (e.g., releasable ratcheting mechanism, etc.) to accomplish this, while in other versions this may not be necessary. Still in other versions, a thumb ring may be biased to seek the distal position where retrieval bag 208 is deployed but closed. In some such versions it may be necessary to hold the thumb ring in its proximal position to maintain retrieval bag 208 in an open position. In any of these versions, when retrieval bag 208 is open, a specimen can be placed within.

Once a specimen has been placed within retrieval bag 208, the thumb ring (or other actuating feature) may be advanced distally again, thereby eliminating the force sufficient to maintain buckling arm 212 in the buckled or bent position. Thus, retrieval bag 208 may close upon such distal movement of the thumb ring. In some versions, the resilience of buckling arm 212 may itself cause such distal advancement, such that the thumb ring only needs to be released to close retrieval bag 208. From this point, the specimen retrieval instrument, including retrieval bag 208 and specimen, may be removed from the patient. In particular, the specimen retrieval instrument and retrieval bag 208 may be removed from the patient in accordance with any of the above teachings relating to removal of specimen retrieval instrument 100 and retrieval bag 108. For instance, retrieval bag 208 may include a closure string as discussed above. Similarly, the specimen retrieval instrument may include a ratcheting mechanism as discussed above with respect to specimen retrieval instrument 100. Still various other suitable features, components, configurations, and operabilities that may be incorporated into the specimen retrieval instrument having components shown in FIGS. 9-11 will be apparent to those of ordinary skill in the art in view of the teachings herein.

II. Exemplary Spring Loop

A. Exemplary Continuous Loop with Loose Deployment

Referring now to FIGS. 12-16, parts of another specimen retrieval instrument are shown. This alternative specimen retrieval instrument includes an actuating rod 304, an introducer tube 306, a plug 334, a retrieval bag 308, a support arm 310, and spring loop 312. This alternative specimen retrieval instrument may also include a handle assembly (not shown) that is substantially identical to handle assembly 102 of specimen retrieval instrument 100 discussed above. In operation with retrieval bag 308, support arm 310, and spring loop 312, these components may function similarly to their corresponding components in FIGS. 8-10, e.g. with retrieval bag 308 opening with proximal movement of actuating rod 304, as will be discussed further below.

In an initial position (not shown, but similar to that of FIG. 1), the alternative specimen retrieval instrument of the present example is in a fully retracted configuration. In this configuration, retrieval bag 308, support arm 310, and spring loop 312 are located within introducer tube 306. As will be discussed in greater detail below, this configuration is achieved by a thumb ring (not shown) and actuating rod 304 being in a proximal position relative to components of a handle assembly that is secured to the proximal end of introducer tube 306. When retracted within introducer tube 306, retrieval bag 308 may be rolled up, folded up, wadded up, or have any other suitable configuration within introducer tube 308.

Figure 12:
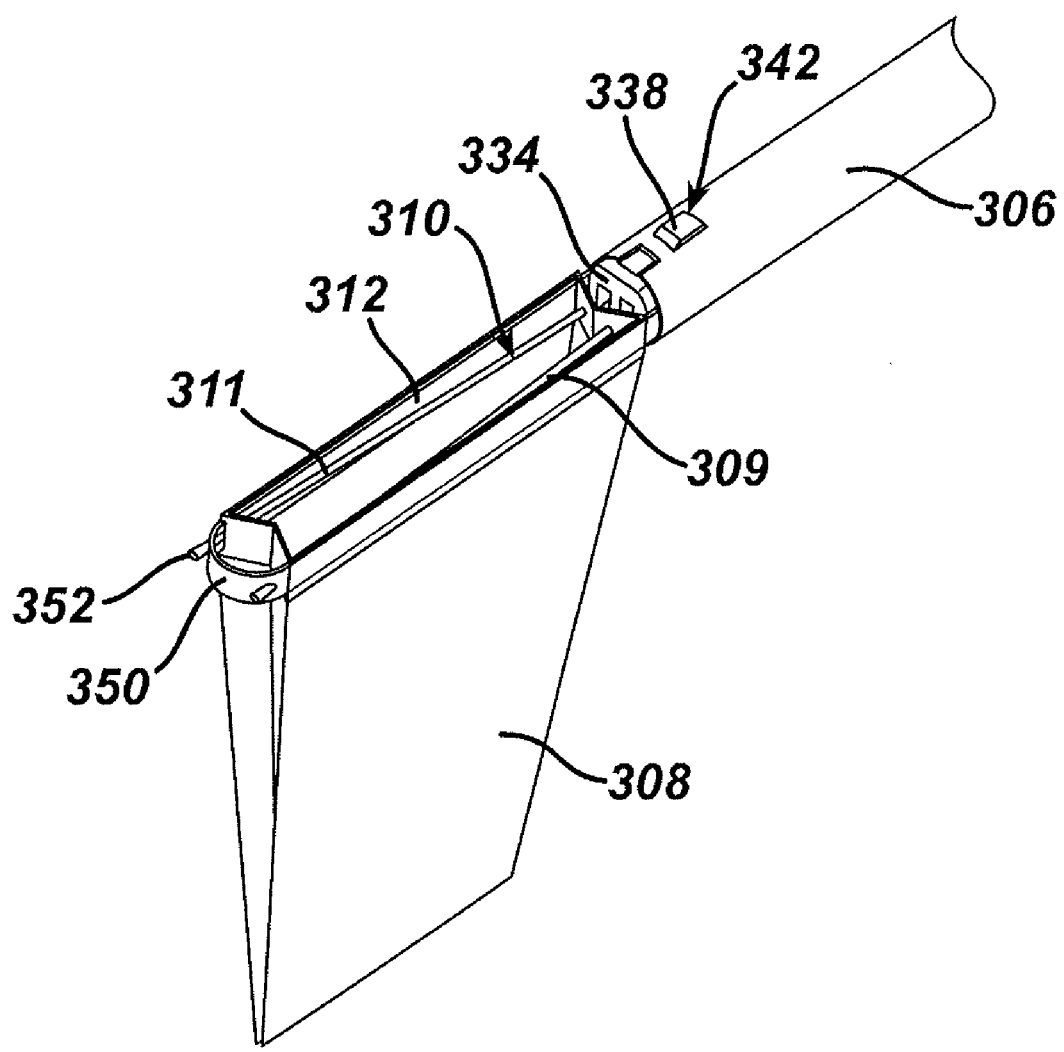
FIG. 12 is a perspective view of the distal end of another exemplary specimen retrieval instrument, having a continuous spring loop and a retrieval bag, with the retrieval bag in a deployed but closed position.
Figure 15:
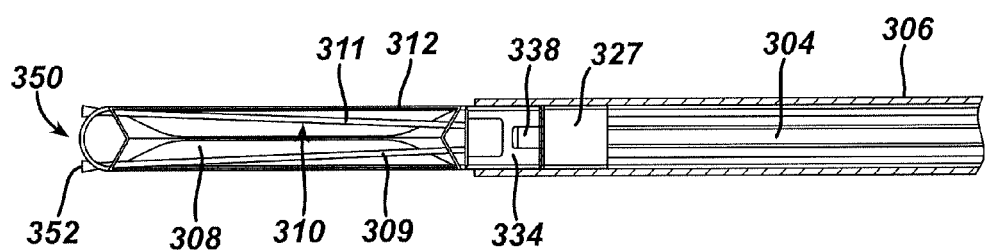
FIG. 15 is a top view of the specimen retrieval instrument of FIG. 12, with the retrieval bag the deployed but closed position and with the introducer tube in cross section.

Referring to FIGS. 12 and 15, the alternative specimen retrieval instrument of the present example is shown with retrieval bag 308, support arm 310, and spring loop 312 deployed but with retrieval bag 308 closed. As will be discussed in greater detail below, this configuration is achieved by the thumb ring and actuating rod 304 being translated to a distal position from the initial proximal position.

Figure 13:
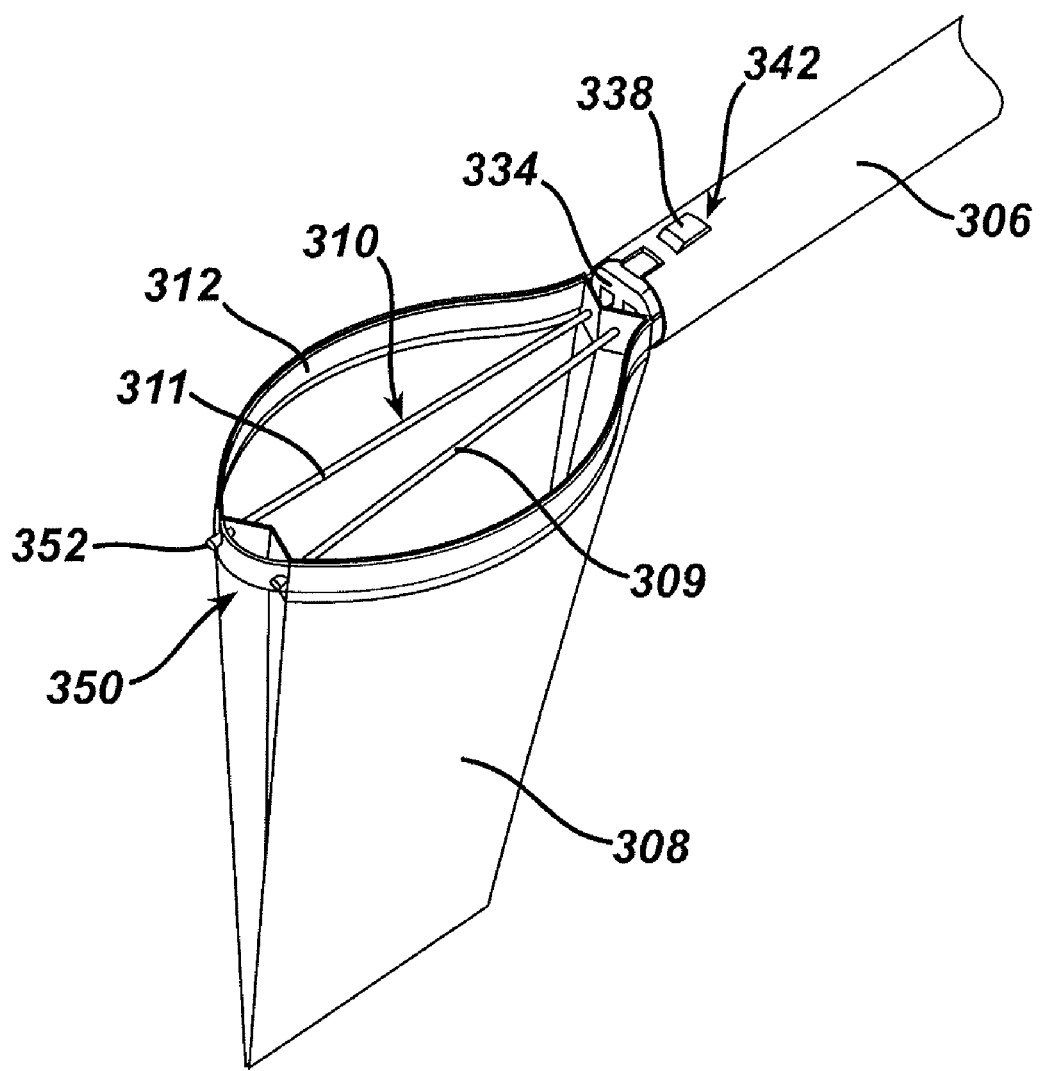
FIG. 13 is a perspective view of the specimen retrieval instrument of FIG. 12, with the retrieval bag in a deployed and opened position.
Figure 16:
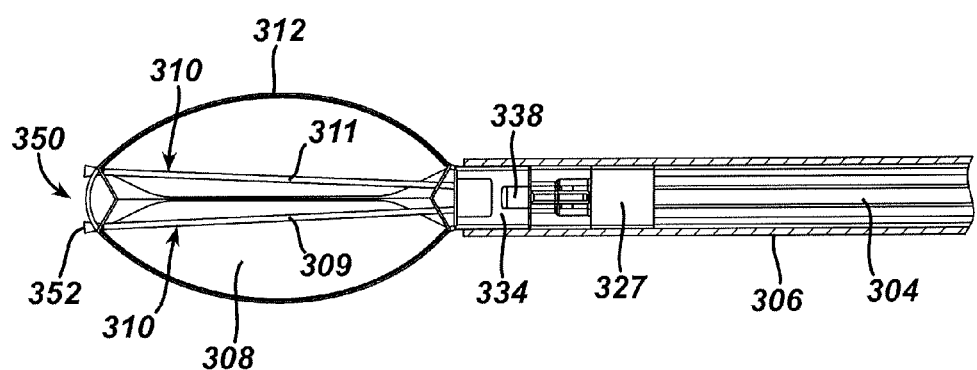
FIG. 16 is a top view of the specimen retrieval instrument of FIG. 12, with the retrieval bag in the deployed and opened position and with the introducer tube in cross section.

Referring to FIGS. 13 and 16, the alternative specimen retrieval instrument of the present example is shown with retrieval bag 308, support arm 310, and spring loop 312 deployed and with retrieval bag 308 opened. As will be discussed in further detail below, this configuration is achieved by the thumb ring and actuating rod 304 being retracted proximally from the distal position shown in FIGS. 12 and 15.

Figure 14:
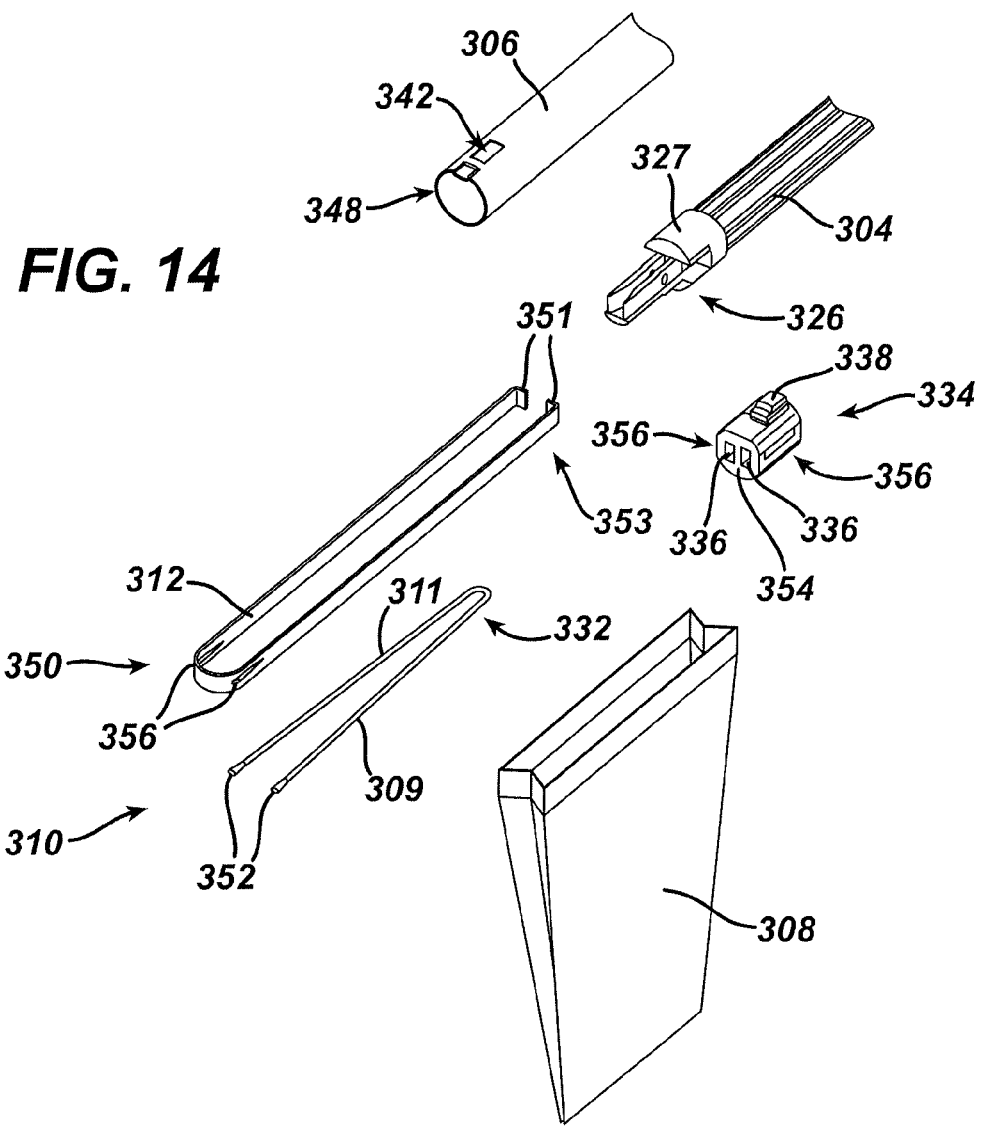
FIG. 14 is an exploded perspective view of the specimen retrieval instrument of FIG. 12.

Referring to FIGS. 14-16, actuating rod 304 includes distal end 326, which is connected to support arm 310 and spring loop 312. The connection of distal end 326 to support arm 310 is such that support arm 310 moves in unison with actuating rod 304. For example, the distal end 326 of actuating rod 304 may securely grasp or be connected to proximal end 332 of support arm 310. Support arm 310 further comprises rods 309, 311, which extend distally from proximal end 332 of support arm 310. The connection of distal end 326 to spring loop 312 is such that actuating rod 304 may move longitudinally, for at least some distance, relative to spring loop 312. For example, spring loop 312 may have dual L-shaped projections 351 at its proximal end 353. Projections 351 may be configured to contact a block 327 of actuating rod 304. In addition or in the alternative, projections 351 may fixedly secure spring loop 312 to plug 334.

Plug 334 is positioned distal to actuating rod 304. Plug 334 is slidably positioned within introducer tube 306. Plug 334 includes pair of openings 336 configured to permit first and second rods 309, 311 of support arm 310 to extend through plug 334. Further, plug 334 includes divider 354 that separates openings 336. Openings 336 are sized to permit first and second rods 309, 311 to translate relative to plug 334 as will be described in greater detail below. Plug 334 also includes dual recessed tracks 356 configured to securely receive respective corresponding portions of spring loop 312. In the present example, spring loop 312 is secured to plug 334 such that spring loop 312 and plug 334 translate unitarily relative to introducer tube 306. As will be described in greater detail below, actuating rod 304, buckling arm support arm 310, plug 334, and spring loop 312 all translate distally together relative to introducer tube 106 during initial deployment of retrieval bag 308. However, during opening of deployed retrieval bag 308, actuating rod 304 and support arm 310 translate proximally relative to plug 334 and relative to spring loop 312. In particular, plug 334 and spring loop 312 remain in a fixed longitudinal position relative to introducer tube 306 when retrieval bag 308 is being opened, as will be described in greater detail below.

Plug 334 further includes tab 338 projecting upwardly from plug 334. A recess (not shown) is formed below tab 332 in plug 334. Tab 338 is resiliently biased to project upwardly from plug 334, but under sufficient force, tab 338 may be deflected downwardly to occupy at least part of the recess. Tab 338 is configured to secure the longitudinal position of plug 334 within introducer tube 306 by engaging lateral opening 342 in introducer tube 306 when tab 338 is positioned within introducer tube 306 and aligned with opening 342. Tab 338 includes a sloped distal end and a generally square proximal end, like tab 138 described above in the context of specimen retrieval instrument 100. In some versions, introducer tube 306 may also be provided with a distal locking member (e.g., indentation or inward projection at distal end 348 of introducer tube 306, etc.), which may be configured to abut a distal end of plug 334 such that the distal locking member prevents plug 334 from exiting introducer tube 306 during deployment and opening of retrieval bag 308.

As shown in FIGS. 12-16, first and second rods 309, 311 of support arm 310 include respective distal ends 352. Furthermore, spring loop 312 includes openings 356 at its distal end 350, with openings 356 being configured to receive distal ends 352 of first and second rods 309, 311. The configuration of openings 356 and distal ends 352 may be such that first and second rods 309, 311 remain securely connected with spring loop 312. For instance, distal ends 352 may have a diameter greater than openings 356. Other suitable ways to securely connect support arm 310 to spring loop 312 will be apparent to those of ordinary skill in the art in view of the teachings herein.

Spring loop 312 of the present example is resiliently biased to assume the substantially elongate configuration as shown in FIGS. 12 and 15. However, the properties of spring loop 312 are such that spring loop 312 is configured to buckle and deform to a substantially round configuration as shown in FIGS. 13 and 16 when rods 309, 311 pull proximally on distal end 350 of spring loop 312 while the longitudinal position of proximal end 353 remains substantially fixed. Spring loop 112 may be formed of any suitable material or combination of materials, including but not limited to metal (e.g., stainless steel, nitinol, steel spring alloys, copper spring alloys, etc.), plastic, and/or metal reinforced plastic.

Retrieval bag 308 is secured to spring loop 312 in the present example. In particular, retrieval bag 308 is substantially closed when has a substantially elongate configuration as shown in FIGS. 12 and 15. However, retrieval bag 308 is opened when spring loop 312 buckles to have a substantially round configuration as shown in FIGS. 13 and 16 and as will be described in greater detail below. By way of example only, spring loop 312 may be inserted through one or more sleeves, slots, pockets, loops, slits, etc., formed in retrieval bag 308. Various suitable ways in which retrieval bag 308 may be secured to spring loop 312 will be apparent to those of ordinary skill in the art in view of the teachings herein.

In use, the alternative specimen retrieval instrument of the present example may initially have an arrangement where retrieval bag 308 is disposed within introducer tube 306, and a thumb ring and actuating rod 304 are at a proximal position. In this arrangement, the distal portion of the specimen retrieval instrument may be inserted within a patient through a suitable incision opening or access port created by a trocar or some other device. By way of example only, introducer tube 306 may present an outer diameter that is between approximately 5 mm (inclusive) and approximately 15 mm (inclusive) (e.g., approximately 10 mm, etc.). Alternatively, introducer tube 306 may have any other suitable dimensions. Once positioned within the patient, retrieval bag 308 may be deployed from within introducer tube 306 by pushing actuating rod 304 distally. This action drives plug 334 distally causing retrieval bag 308, support arm 310, and spring loop 312 to emerge from open distal end 348 of introducer tube 306. At about the same time retrieval bag 308 is deployed, tab 338 of plug 334 aligns with opening 342 of introducer tube 306. When aligned, tab 338 engages opening 342 due to tab 338 being resiliently biased to project upwardly from plug 334. Once retrieval bag 308 has been deployed, specimen retrieval instrument 300 may have the arrangement shown in FIGS. 12 and 15.

With the alternative specimen retrieval instrument of the present example in position within the patient and having retrieval bag 308 deployed (with the longitudinal position of plug 334 and spring loop 312 being substantially locked in place relative to introducer tube 306), actuating rod 304 may be pulled proximally within introducer tube 306, which may also retract support arm 310 proximally. As support arm 310 moves proximally with actuating rod 304, support arm 310 applies a proximal force to distal end 350 of spring loop 312. Furthermore, with spring loop 312 secured to plug 334, and plug 334 engaged via tab 338 with opening 342 of introducer tube 306, proximal end 353 of spring loop 312 is substantially fixed in place longitudinally. The properties of spring loop 312 are such that spring loop 312 buckles outwardly when a sufficient force is applied in a proximal direction to distal end 350 of spring loop 312. When spring loop 312 buckles outwardly, retrieval bag 308 opens as noted above.

In some versions, retrieval bag 308 is maintained in an open position by a thumb ring (or other actuating feature) being configured to remain in a proximal position. Some such versions may use various biasing or locking means (e.g., releasable ratcheting mechanism, etc.) to accomplish this, while in other versions this may not be necessary. Still in other versions, a thumb ring may be biased to seek the distal position where retrieval bag 308 is deployed but closed. In some such versions it may be necessary to hold the thumb ring in its proximal position to maintain retrieval bag 308 in an open position. In any of these versions, when retrieval bag 308 is open, a specimen can be placed within.

Once a specimen has been placed within retrieval bag 308, the thumb ring (or other actuating feature) may be advanced distally again, thereby eliminating the force sufficient to maintain spring loop 312 in the buckled or bent position. Thus, retrieval bag 308 may close upon such distal movement of thumb ring 314. In some versions, the resilience of spring loop 312 may itself cause such distal advancement, such that the thumb ring only needs to be released to close retrieval bag 308. From this point, specimen retrieval instrument 300, including retrieval bag 308 and specimen, may be removed from the patient. In particular, the specimen retrieval instrument and retrieval bag 308 may be removed from the patient in accordance with any of the above teachings relating to removal of specimen retrieval instrument 100 and retrieval bag 108. For instance, retrieval bag 308 may include a closure string as discussed above. Similarly, the specimen retrieval instrument may include a ratcheting mechanism as discussed above with respect to specimen retrieval instrument 100. Still various other suitable features, components, configurations, and operabilities that may be incorporated into the specimen retrieval instrument having components shown in FIGS. 12-16 will be apparent to those of ordinary skill in the art in view of the teachings herein. By way of example only, rods 309, 311 and/or other portions of support arm 310 may be substituted with cables, strings, other flexible members, and/or a variety of other components. As another merely exemplary variation, opening of retrieval bag 308 may be effected by substantially securing the longitudinal position of support arm 310 relative to introducer tube 306, then advancing spring loop 312 distally relative to introducer tube 306 to cause spring loop 312 to buckle and open retrieval bag 308. For instance, support arm 310 may be unitarily secured to plug 334, spring loop 312 may be unitarily secured to actuating rod 304, and a spring 128 may be positioned between the distal end of actuating rod 304 and the proximal face of plug 334.

B. Exemplary Rigid Distal End Loop with Flat Deployment

Figure 17:
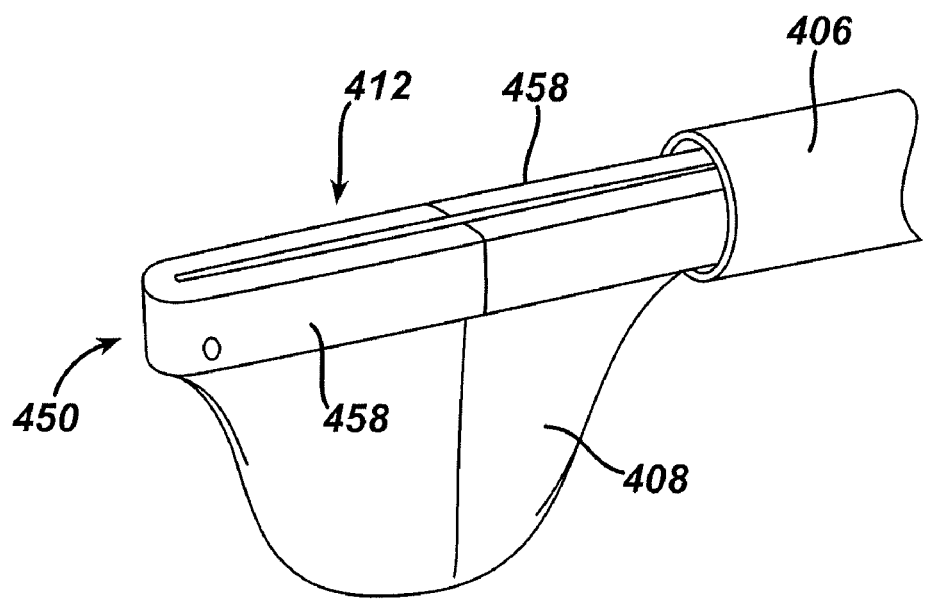
FIG. 17 is a perspective view of the distal end of another exemplary specimen retrieval instrument, having a spring loop with a rigid distal end and a retrieval bag, with the retrieval bag in a deployed but closed position.
Figure 18:
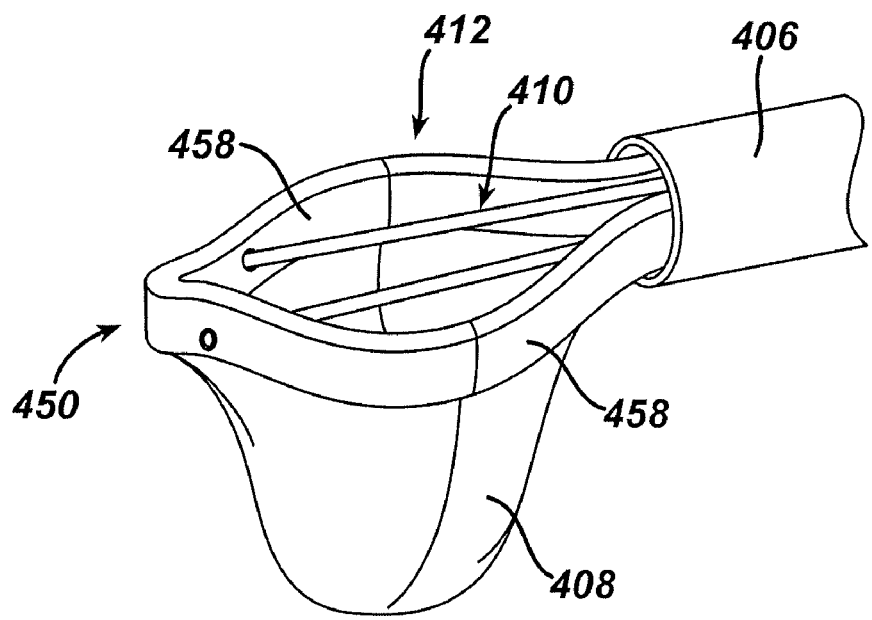
FIG. 18 is a perspective view of the specimen retrieval instrument of FIG. 17, with the retrieval bag in a deployed and opened position.

Referring now to FIGS. 17-18, parts of another specimen retrieval instrument are shown. With the exception of spring loop 412, the components of this exemplary alternative specimen retrieval instrument are identical to those described above with respect to FIGS. 12-16. The version of spring loop 412 allows for a substantially flatter deployment of spring loop 412, retrieval bag 408, and support arm 410. This substantially flat deployment is achieved by spring loop 412 having a rigidly apposed distal end 450. With this configuration, spring loop 412 has a closed bias such that spring loop 412 deploys flat and remains in this flat and closed orientation until proximal force is applied to distal end 450 of spring loop 412. The longitudinal position of the proximal portion of spring loop 412 relative to introducer tube 406 may be selectively secured by a plug identical to plug 334 described above. Alternatively, any other suitable components or features may be used.

As described above, proximal movement of an actuating rod and connected support arm 410 (which could be substituted with strings, cables, other flexible members, etc.) cause a proximal force to be applied to distal end 450 of spring loop 412. This proximal force causes spring loop 412 to open retrieval bag 408, which is attached to spring loop 412, for receiving a specimen. As seen in FIGS. 17-18, it will be appreciated that the sides 458 of spring loop 412 are capable of buckling or bending under a sufficient proximal force, whereas rigid distal end 450 remains in a substantially apposed configuration under the same proximal force.

III. Exemplary Retraction Deployment Mechanism

Figure 19:
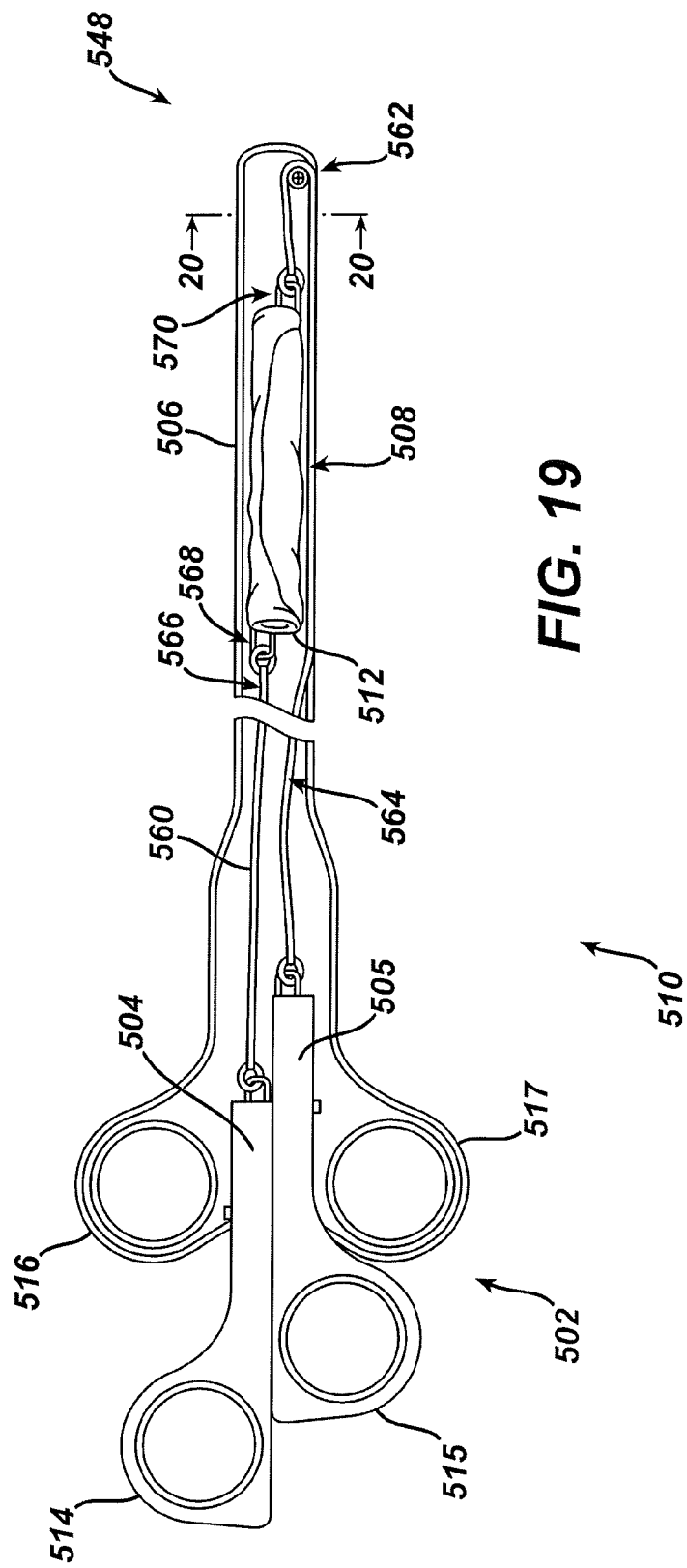
FIG. 19 is a side cross section view of another exemplary specimen retrieval instrument, having a retraction deployment mechanism.
Figure 20:
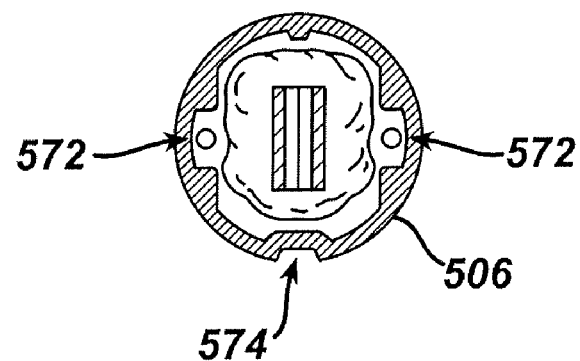
FIG. 20 is a cross section view of the specimen retrieval instrument of FIG. 19 taken along line 20-20.
Figure 21:
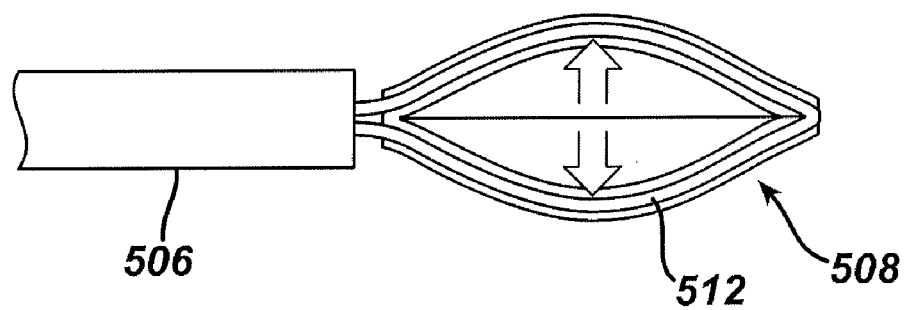
FIG. 21 is a top view of the distal end of the specimen retrieval instrument of FIG. 19, with the retrieval bag deployed and opened.

Referring now to FIGS. 19-21, yet another exemplary specimen retrieval instrument 500 is shown. Specimen retrieval instrument 500 provides distal deployment of retrieval bag 508 by retracting handle assembly 502 components through use of a pulley mechanism. More specifically, specimen retrieval instrument 500 includes handle assembly 502, which includes finger rings 514, 515, 516, and 517. Finger rings 514, 515 are connected to respective actuating rods 504, 505. Actuating rods 504, 505 are connected to opposite ends of cable 560. Intervening in the length of cable 560 and connected with cable 560 is spring loop 512 and retrieval bag 508. The connection of spring loop 512 to cable 560 occurs at a first connection point 568 and second connection point 570 of spring loop 512. Near distal end 548 of introducer tube 506 is pulley roller 562, around which cable 560 travels. Introducer tube 506 may be sized for insertion through a trocar port. By way of example only, introducer tube 506 may present an outer diameter that is between approximately 5 mm (inclusive) and approximately 15 mm (inclusive) (e.g., approximately 10 mm, etc.). Alternatively, introducer tube 506 may have any other suitable dimensions.

In use, finger ring 515 is moved proximally away from distal end 548 of introducer tube 506. This movement causes a corresponding proximal movement of actuating rod 505. In response to the movement of actuating rod 505, a first portion 564 of cable 560 moves proximally while a second portion 566 of cable 560 moves distally, with pulley roller 562 providing the change in direction. As second portion 566 of cable 560 moves distally, spring loop 512 and retrieval bag 508 are advanced toward distal end 548 of introducer tube 506. Upon reaching open distal end 548 of introducer tube 506, the spring bias of spring loop 512 causes spring loop 512 to open, thereby also opening retrieval bag 508. During the action of spring loop 512 opening, spring loop 512 pivots about the second connection point 570 as the second connection point 570 wraps about pulley roller 562. At or about the same time, first connection point 568 advances from within introducer tube 506 past pulley roller 562 and past second connection point 570 such that when spring loop 512 is open, first connection point 568 is distal to second connection point 570. This action of spring loop 512 opening drives second cable portion 566 distally along with actuating rod 504 and finger ring 514.

Once a specimen has been collected in retrieval bag 508, retrieval bag 508 may be closed by proximal movement of finger ring 514. This action causes actuating rod 504 to move proximally along with second cable portion 566 and first connection point 568. The proximal movement of first connection point 568 causes spring loop 512 to close as first connection point 568 approaches open distal end 548 of introducer tube 506. From this point, specimen retrieval instrument 500, including retrieval bag 508 and specimen, may be removed from the patient.

Other optional features of specimen retrieval instrument 500 may include internal longitudinal guides 572 as shown in FIG. 20. Guides 572 are configured to aid in maintaining spring loop 512 and retrieval bag 508 in a furled and closed position within introducer tube 506 during deployment. Also, specimen retrieval instrument 500 may be provided with a channel 574 configured to guide cable 560 during use. For instance, as shown in FIGS. 19 and 20, channel 574 may be located along an underside of introducer tube 506 and providing a path for first cable portion 564 during operation of specimen retrieval instrument 500. Based on the teachings herein, those of ordinary skill in the art will appreciate other modifications and features that may aid in operating specimen retrieval instrument 500.

IV. Exemplary Retrieval Bag Modifications

A. Exemplary Rotating Aperture Closure

Figure 22:
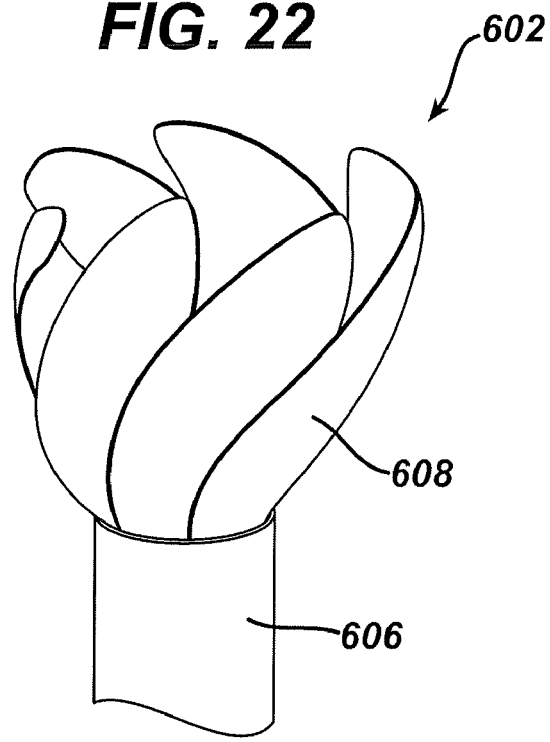
FIG. 22 is a perspective view of the distal end of another exemplary specimen retrieval instrument, with specimen capture petals in a deployed and open configuration.
Figure 23:
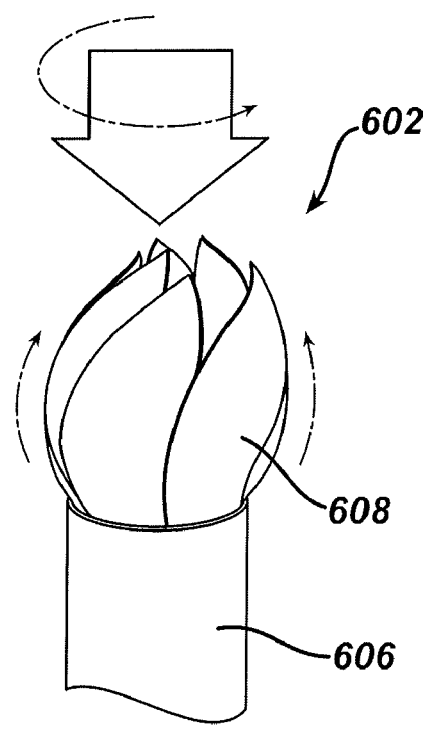
FIG. 23 is a perspective view of the specimen retrieval instrument of FIG. 22, with the specimen capture petals in a closed configuration.

FIGS. 22-23 show parts of yet another exemplary specimen retrieval instrument. This alternative specimen retrieval instrument comprises a tissue capture feature 602 and an introducer tube 606. Tissue capture feature 602 of this example comprises a plurality of interleaved or overlapping petals 608. Petals 608 may be formed of silicone or any other suitable material or combination of materials. The overlapping configuration of petals 608 is similar to blades or leaves of a camera lens iris, albeit extending in three dimensions instead of simply lying along a plane. In particular, petals 608 are rotatable relative to introducer tube 606 to selectively open or close tissue capture feature 602. For instance, an actuation rod (not shown) may be disposed through introducer tube 606, and may be both translatable and rotatable relative to introducer tube 606. Such an actuation rod may thus be used to selectively open and close tissue capture feature 602 by rotating petals 608, to selectively retract petals 608 within introducer tube 606, and to selectively extend petals 608 from introducer tube 606. Petals 608 and/or introducer tube 606 may include one or more grounding features that provide a pivotal connection between the proximal portion of each petal 608 and the distal portion of introducer tube 606, allowing petals 608 to be rotated about such respective pivotal connections to selectively open and close tissue capture feature.

In use, introducer tube 606 may be inserted in a patient through a trocar or other device, with tissue capture feature 602 closed and/or retracted within introducer tube 606. By way of example only, introducer tube 606 may present an outer diameter that is between approximately 5 mm (inclusive) and approximately 15 mm (inclusive) (e.g., approximately 10 mm, etc.). Alternatively, introducer tube 606 may have any other suitable dimensions. Once tissue capture feature 602 is in the patient, the actuator may be rotated to open tissue capture feature 602 to the configuration shown in FIG. 22. A tissue specimen may be placed in the open tissue capture feature 602. In some versions, introducer tube 606 includes and articulation joint or articulation section near the distal end of introducer tube 606, allowing tissue capture feature to more easily be positioned to reduce the likelihood of tissue specimens falling out of tissue capture feature 602 while tissue capture feature 602 is open. After one or more tissue specimens are placed in tissue capture feature 602, the actuator may be rotated to close tissue capture feature 602 as shown in FIG. 23. With tissue capture feature 602 closed, tissue capture feature 602 and introducer tube 606 may be withdrawn from the patient.

In some versions, petals 608 are resiliently biased to assume the open configuration shown in FIG. 22. In some such versions, the surgeon need only advance tissue capture feature 602 distally to sufficiently expose tissue capture feature 602 relative to introducer tube 606 in order for tissue capture feature 602 to open. Still other suitable components, features, configurations, and operabilities will be apparent to those of ordinary skill in the art in view of the teachings herein.

B. Exemplary Wire Rim Closure

Figure 24:
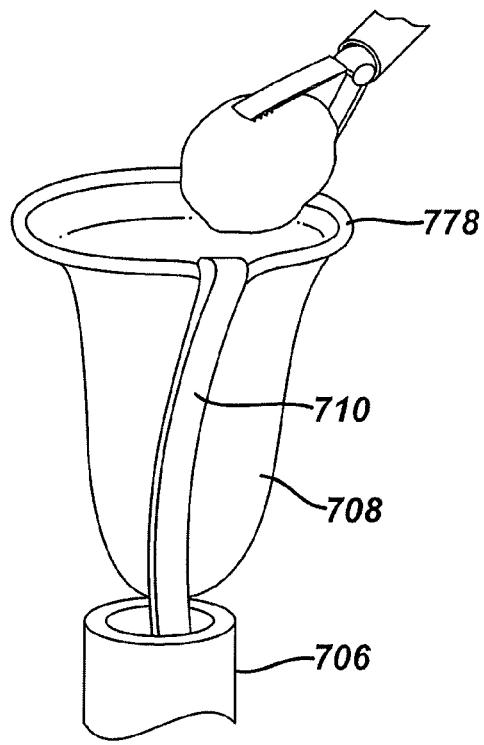
FIG. 24 is a perspective view of the distal end of another exemplary specimen retrieval instrument, having a retrieval bag for use with a retractable wire rim closure mechanism, with the retrieval bag in a deployed and opened configuration.
Figure 25:
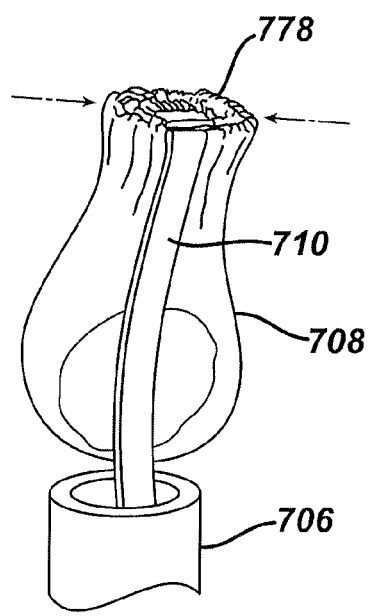
FIG. 25 is a perspective view of the specimen retrieval instrument of FIG. 24, with the retrieval bag in a deployed and closed configuration.

FIGS. 24-25 show parts of yet another exemplary specimen retrieval instrument. This alternative specimen retrieval instrument comprises an introducer tube 706, a retrieval bag 708, a support arm 710, and a wire rim 778. Wire rim 778 is secured to the end of retrieval bag 708 where retrieval bag 708 opens and closes. Wire rim 778 further continues within support arm 710 and is in communication with a trigger mechanism (not shown) or actuating rod (not shown).

In operation, retrieval bag 708 and support arm 710 may be initially positioned within introducer tube 706. Deployment of retrieval bag 708 and support arm 710 may be accomplished by any of the above-described manners. Once deployed, retrieval bag 708 may open under a spring bias of wire rim 778. Alternatively, retrieval bag 708 may be opened by either actuating trigger mechanism (not shown) or rotating actuating rod (not shown) through a corresponding rotation of thumb ring (not shown). Trigger mechanism (not shown) or actuating rod (not shown) are configured to retract and release wire rim 778 thereby causing wire rim 778 to open retrieval bag 708 when wire rim 778 is released, or close retrieval bag 708 when wire rim 778 is retracted. Once a specimen has been placed within retrieval bag 708, the specimen retrieval instrument, including retrieval bag 708 and specimen, may be removed from the patient by any of the means described above. Still other suitable components, features, configurations, and operabilities will be apparent to those of ordinary skill in the art in view of the teachings herein.

C. Exemplary Segmented Wire Closure

Figure 26:
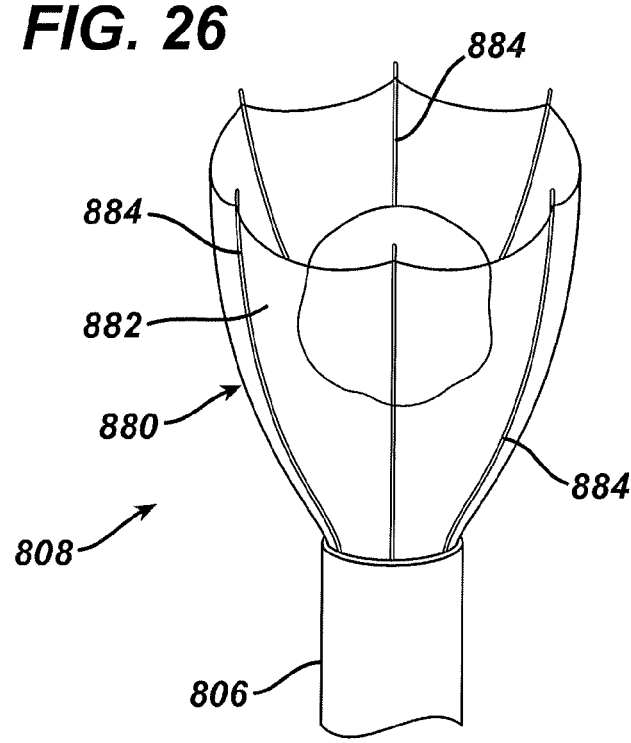
FIG. 26 is a perspective view of the distal end of another exemplary specimen retrieval instrument, having a retrieval bag with a segmented wire closure mechanism, with the retrieval bag in a deployed and opened configuration.
Figure 27:
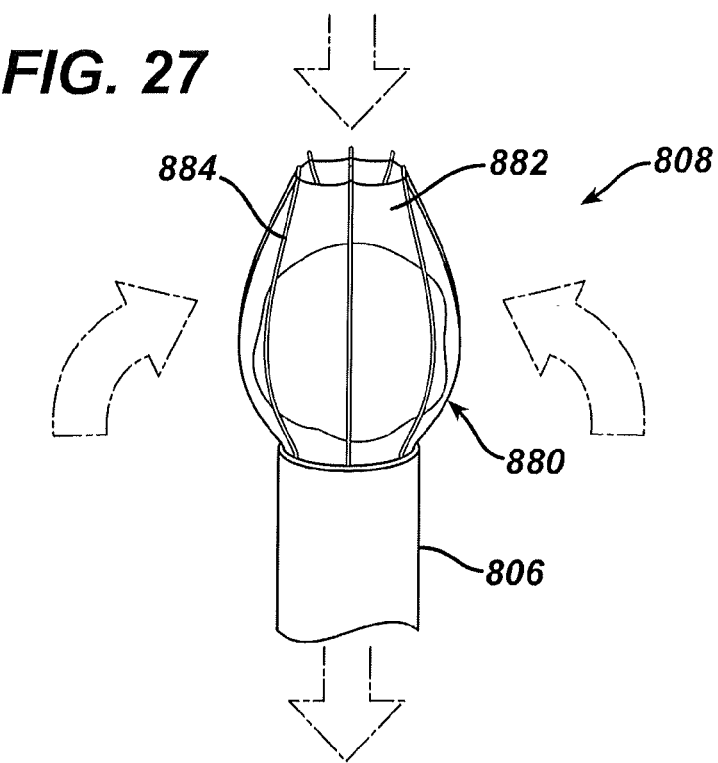
FIG. 27 is a perspective view of the specimen retrieval instrument of FIG. 25, with the retrieval bag in a deployed and closed configuration.

FIGS. 26-27 show parts of yet another exemplary specimen retrieval instrument. This alternative specimen retrieval instrument comprises an introducer tube 806 and a retrieval bag 808, which includes segments 880 defined by webbing 882 and flexible wires 884.

In operation, retrieval bag 808 may be initially positioned within introducer tube 806. Deployment of retrieval bag 808 may be accomplished by any of the above-described manners. Once deployed, retrieval bag 808 may open under a resilient bias of flexible wires 884. Once a specimen has been placed within retrieval bag 808, retraction of an actuating rod (not shown) will cause segments 880 to close around the specimen. In some merely illustrative variations, segments 880 are closed by the operator pulling on a cable, string, or other component instead of an actuating rod. From this point, the specimen retrieval instrument, including retrieval bag 808 and specimen, may be removed from the patient by any of the means described above. As another merely illustrative variation, flexible wires 884 may resiliently bias retrieval bag 808 to a closed position. In some such versions, advancement of an actuating rod may cause segments 880 to open to allow receipt of a tissue specimen. Still other suitable components, features, configurations, and operabilities will be apparent to those of ordinary skill in the art in view of the teachings herein.

While several specimen retrieval instruments, and components thereof, have been discussed in detail above, it should be understood that the components, features, configurations, and methods of using the specimen retrieval instruments discussed are not limited to the contexts provided above. In particular, components, features, configurations, and methods of use described in the context of one of the specimen retrieval instruments may be incorporated into any of the other specimen retrieval instruments. One merely exemplary additional feature that may be provided in any of the specimen retrieval instruments described herein is a distal locking member of an introducer tube. Such a distal locking member may be configured to abut a distal end of any of the described plugs, such that the distal locking member prevents over-insertion when deploying a retrieval bag. Another merely exemplary additional feature that may be provided in any of the specimen retrieval instruments described herein includes retrieval bags having various sizes and geometries. For example, some specimen retrieval instruments may be designed with small, medium, or large retrieval bags. Also for example, some tissue retrieval instruments may use retrieval bags having pleats and/or gussets that allow for expansion when holding larger specimens. It should also be understood that any of the specimen retrieval instruments and tissue retrieval bags described herein may be capable of receiving tissue specimens and removing tissue specimens from a patient without such tissue specimens needing to be morcellated or otherwise reduced in size before being received and removed by the specimen retrieval instrument and bag. Still other additional and alternative suitable components, features, configurations, and methods of using the specimen retrieval instruments will be apparent to those of ordinary skill in the art in view of the teachings herein.

Other features and modifications that will be appreciated based on the teachings herein involve methods of attaching a retrieval bag to any of the various arms and loops or other components of a specimen retrieval instrument described above. For example, retrieval bags may be configured with one or more sleeves, slots, pockets, loops, slits, etc., for receiving any of the various arms and loops described above. In other versions, retrieval bags may be connected to any of the various arms, loops, or other components using suitable mechanical or chemical means. It will further be appreciated that in some versions the retrieval bag may be detachable from the other components of the specimen retrieval instrument, while in some other versions the retrieval bag may be inseparable from the specimen retrieval instrument. Still other additional and alternative suitable components, features, configurations, and methods of attaching retrieval bags with the other components of a specimen retrieval instrument will be apparent to those of ordinary skill in the art in view of the teachings herein.

As noted above, the various versions of specimen retrieval instruments described herein, including but not limited to the various versions of retrieval bags described herein, may be used in a conventional endoscopic procedure that includes the insertion of the introducer tube or other component through a small opening, e.g., an incision, natural orifice, or trocar access port, etc. Of course, specimen retrieval instruments described herein may be used in conjunction with any other suitable surgical or medical procedure, such as endoscopic/laparoscopic procedures, open surgical procedures, or robotic-assisted surgery, etc. Still other various settings and combinations in which specimen retrieval instruments described herein may be used will be apparent to those of ordinary skill in the art in view of the teachings herein.

While several retrieval bags and deployment mechanisms have been discussed in detail above, it should be understood that the components, features, configurations, and methods of using the bags and deployment mechanisms discussed are not limited to the contexts provided above. In particular, components, features, configurations, and methods of use described in the context of one of the retrieval bags may be incorporated into any of the other retrieval bags. One merely exemplary additional feature that may be provided in any of the retrieval bags described herein is one or more weld lines. Such weld lines may be intermittent or continuous along the length of the bag. Such weld lines, offering alternating areas of stiffness along the surface of the bag, may enhance the closure of a bag due to the tendency of areas of lesser stiffness to buckle, deform, or fold. In this way, a retrieval bag may be forced or encouraged to buckle or fold in a desired manner as the bag is closed. Still other additional and alternative suitable components, features, configurations, and methods of using the above-described retrieval devices will be apparent to those of ordinary skill in the art in view of the teachings herein.

While the tissue retrieval instruments of the above-described examples are actuated manually by advancing a thumb ring distally relative to finger rings or in some other manual fashion, etc., it should be understood that any of the tissue retrieval instruments described herein may instead be actuated in any other suitable fashion. By way of example only, a tissue retrieval instrument may instead be actuated electromechanically (e.g., using one or more electrical motors, solenoids, etc.), pneumatically, and/or hydraulically. Various suitable ways in which such alternative forms of actuation may be provided in a tissue retrieval instrument will be apparent to those of ordinary skill in the art in view of the teachings herein. Similarly, various other suitable ways in which a tissue retrieval instrument may be actuated will be apparent to those of ordinary skill in the art in view of the teachings herein.

It should be understood that any of the retrieval bags described herein may have various types of construction. By way of example only, any of the retrieval bags described herein may be constructed from at least one layer of an elastomeric or polymeric material such as but not limited to polyurethane, polyethylene, polypropelene, polyester (Duralar), Poly-isoprene, silicone, vinyl, or a polytetrafluroethyelene (Teflon®). For example, any retrieval bag described herein may comprise a single layer of elastomeric or polymeric material. Alternatively, any retrieval bag described herein may be formed of two or more layers of material. For instance, two or more layers of a retrieval bag wall may be aligned and joined together by adhesives, heat welding, heat staking, RF welding, ultrasonically welding, or other suitable method of attachment. Any retrieval bag described herein may also be cut at an angle to provide a taper or special shapes suitable for specific organs of body (e.g., tissue shapes, etc.), which may facilitate removal of the retrieval bag from a patient. Furthermore, any retrieval bag described herein may incorporate flexible metal meshes, thermoformed plastic meshes, fabrics, or aramid fibers such as Kevlar® for reinforcement. Still other suitable materials that may be used to form retrieval bags as described herein, including combinations of materials, will be apparent to those of ordinary skill in the art in view of the teachings herein. Similarly, various other suitable compositions of the walls of the retrieval bags described herein, including but not limited to various structures, components, and features that may be incorporated into the walls of the retrieval bags described herein, will be apparent to those of ordinary skill in the art in view of the teachings herein.

In any of the above described tissue retrieval instruments, the tissue retrieval bag may include a fold-over flap (not shown) for closing the bag. For instance, such a fold-over flap may be used instead of (or in addition to) using a string to effect closure of the bag. Such a fold-over flap may include an adhesive (e.g., pressure sensitive adhesive, etc.) that substantially keeps the flap in a closed position after the flap has been moved to a closed position. A peel-away strip or similar feature may be used to cover such an adhesive before the flap is closed. A conventional grasping instrument or other type of device may be used to peel the peel-away strip and/or close the flap over the mouth of the bag while the bag is still inside the patient. In some other variations, a tissue retrieval bag may be formed at least in part of a material that provides significant static adhesion or other type of adhesion to itself. For instance, the interior surfaces of the tissue retrieval bag may be configured to adhere to each other and/or to adhere to tissue/objects placed in the bag, to reduce the likelihood of tissue/objects in the bag falling out of the bag. In some such versions, a closure string is omitted. Other suitable variations of a tissue retrieval bag will be apparent to those of ordinary skill in the art in view of the teachings herein.

Versions of the devices disclosed herein have application in conventional endoscopic and open surgical instrumentation as well as application in robotic-assisted surgery.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A surgical instrument for removal of material from a patient, the surgical instrument comprising:
   a. a retrieval bag configured to open and close;
   b. a first arm having a distal end and a proximal end, wherein the first arm is associated with the retrieval bag;
   c. a second arm having a distal end and a proximal end, wherein the second arm is associated with the retrieval bag, wherein the distal end of the second arm is in communication with the distal end of the first arm, and wherein the second arm is operable to move away from the first arm to open the retrieval bag;
   d. a plug, wherein the plug is associated with the first and second arms, wherein the plug is fixedly secured to the first arm and wherein the plug is slidable relative to the second arm; and
   e. an actuator in communication with at least one of the first arm or the second arm, wherein the actuator is operable to translate longitudinally to urge the second arm away from the first arm to open the retrieval bag;
   wherein the retrieval bag is opened upon distal movement of the actuator;
   wherein the actuator comprises an actuating rod having a recess and a spring near a distal end of the actuating rod, wherein the spring extends longitudinally within the recess;
   wherein the spring is configured to maintain spatial separation between the plug and a distal end of the actuating rod.

2. The surgical instrument of claim 1 further comprising an introducer tube, wherein the actuator comprises an actuating rod configured to fit within the introducer tube.

3. The surgical instrument of claim 2, wherein the actuating rod is movable to a proximal position where the retrieval bag is retracted within the introducer tube.

4. The surgical instrument of claim 3, wherein the actuating rod is movable to an intermediate distal position where the retrieval bag is deployed from the introducer tube in a closed position.

5. The surgical instrument of claim 4, wherein the actuating rod is movable to a fully distal position where the retrieval bag is in an open position.

6. The surgical instrument of claim 2, wherein the first arm further comprises at least one tab projecting laterally relative to a longitudinal axis defined by the introducer tube.

7. The surgical instrument of claim 2 further comprising a handle assembly, wherein the handle assembly is operable to translate the actuating rod within the introducer tube.

8. The surgical instrument of claim 7, wherein the plug further comprises a tab projecting laterally from the plug.

9. The surgical instrument of claim 8, wherein the introducer tube comprises a lateral opening near a distal end of the introducer tube, wherein the opening is configured to engage the tab of the plug during deployment of the retrieval bag.

10. The surgical instrument of claim 9, wherein the tab of the plug is configured to engage the lateral opening of the introducer tube when the actuating rod is in an intermediate distal position.

11. The surgical instrument of claim 7, wherein the handle assembly comprises a thumbring and at least one finger ring, wherein the thumbring is moveable relative to the at least one finger ring.

12. The surgical instrument of claim 11, wherein the handle assembly comprises two finger rings.

13. The surgical instrument of claim 11, wherein the actuating rod is configured to move in unison with the thumbring.

14. The surgical instrument of claim 1, wherein the proximal end of the first arm is configured to contact the spring and compress the spring as the actuating rod translates distally.

15. The surgical instrument of claim 14, wherein the second arm moves in unison with the actuating rod, wherein the second arm flexes away from the first arm as the actuating rod translates distally.

16. A surgical instrument for removal of material from a patient, the surgical instrument comprising:
   a. a retrieval bag configured to open and close;
   b. a first arm having a distal end and a proximal end, wherein the first arm is associated with the retrieval bag;
   c. a second arm having a distal end and a proximal end, wherein the second arm is associated with the retrieval bag, wherein the distal end of the second arm is in communication with the distal end of the first arm, and wherein the second arm is operable to move away from the first arm to open the retrieval bag;
   d. an actuator in communication with at least one of the first arm or the second arm, wherein the actuator is operable to translate longitudinally to urge the second arm away from the first arm to open the retrieval bag, wherein the actuator comprises a longitudinal recess; and
   e. a resilient member extending within the longitudinal recess, wherein the resilient member is configured to engage the proximal end of the first arm to resiliently bias the proximal end of the first arm away from the actuator.

17. A surgical instrument for removal of material from a patient, the surgical instrument comprising:
   a. a retrieval bag configured to open and close;
   b. a first arm having a distal end and a proximal end, wherein the first arm is associated with the retrieval bag;
   c. a second arm having a distal end and a proximal end, wherein the second arm is associated with the retrieval bag, wherein the distal end of the second arm is in communication with the distal end of the first arm, and wherein the second arm is operable to move away from the first arm to open the retrieval bag;
   d. an introducer tube comprising a passageway, wherein the first arm and the second arm are configured to extend through the passageway of the introducer tube;
   e. an actuating rod configured to fit within the passageway of the introducer tube, wherein the actuating rod is in communication with at least one of the first arm or the second arm, wherein the actuating rod is operable to translate longitudinally to urge the second arm away from the first arm to open the retrieval bag, wherein the actuating rod comprises a longitudinal recess; and
   f. a resilient member extending within the longitudinal recess, wherein the resilient member is parallel with a longitudinal axis defined by the introducer tube, wherein the resilient member is positioned proximally to the first arm, the resilient member configured to engage the proximal end of the first arm to resiliently bias the proximal end of the first arm away from the actuator.

* * * * *